United States Patent [19]

Kensil et al.

[11] Patent Number: 5,057,540

[45] Date of Patent: Oct. 15, 1991

[54] SAPONIN ADJUVANT

[75] Inventors: Charlotte A. Kensil, Milford; Dante J. Marciani, Hopkinton, both of Mass.

[73] Assignee: Cambridge Biotech Corporation, Worcester, Mass.

[21] Appl. No.: 573,268

[22] Filed: Aug. 27, 1990

Related U.S. Application Data

[63] Continuation of Ser. No. 200,754, May 31, 1988, abandoned, which is a continuation-in-part of Ser. No. 55,229, May 29, 1987, abandoned.

[51] Int. Cl.$^5$ .................. A61K 31/70; A61K 31/705; A61K 39/00
[52] U.S. Cl. ........................................ 514/25; 514/26; 514/33; 514/35; 514/885; 424/88; 424/195.1; 536/4.1; 536/6.3; 536/5
[58] Field of Search ...................... 514/25, 26, 33, 35, 514/885; 424/88, 89, 195.1; 536/4.1, 6.3, 18.1, 127, 128, 5

[56] References Cited

U.S. PATENT DOCUMENTS

| | | | |
|---|---|---|---|
| 4,335,113 | 6/1982 | Combier et al. | 536/18.1 |
| 4,524,067 | 6/1985 | Arichi et al. | 536/18.1 |
| 4,789,702 | 12/1988 | Nunberg | 424/89 |

FOREIGN PATENT DOCUMENTS

| | | | |
|---|---|---|---|
| 0160763 | 3/1984 | Fed. Rep. of Germany | 424/89 |
| 54-132218 | 10/1979 | Japan . | |
| 61-007286A | 1/1986 | Japan . | |
| 0548046 | 8/1977 | U.S.S.R. | 424/89 |

OTHER PUBLICATIONS

Sakuma et al; J. Chromatography, 400:293-5, Jul. 29, 1987.
Dalsgaard, K., *Archive fur die gesamte Virusforshung*, 44:243-254 (1974).
Higuchi et al., *Phytochemistry*, 26 (1):229-235 (1987).
Higuchi and Komori, *Phytochemistry*, 26 (8):2357-2360 (1987).
Dalsgaard, K., *Acta Veterinari Scandinavica* (Suppl.), 69:1-40 (1978).
Scott et al., *Int. Archs Allergy Appl. Immun.*, 77:409-412 (1985).
Higuchi et al., *Phytochemistry*, 27 (4):1165-1168 (1988).
Petermann, H. G. et al., *Chemical Abstracts*, 72:198, 88330c (1970).
Bomford, R., *Int. Archs Allergy Appl. Immun.*, 63:170-177 (1980).
Nagasawa et al., *Chem. Pharm. Bull.*, 28(7):2059-2064, (1980).
Zhou et al., *Chem. Pharm. Bull*, 29 (10):2844-2850 (1981).
Bomford, R., *Int. Archs Allergy Appl. Immun.*, 67:127-131 (1982).
Bomford, R., *Int. Archs Allergy Appl. Immun.*, 75:280-281 (1984).
Morein et al., *Nature*, 308:457-460 (1984).
Strobbe et al., *Arch. Exper. Vet. Med.*, 28:385-392 (1974).
Mostad and Doehl, *J. of Chromatography*, 396:157-168 (1987).
Egerton et al., *Vet. Sci. Comm.*, 2:247-252 (1978).
McColm et al., *Parasite Immun.*, 4:337-347 (1982).
Kartnig et al., *Planta Medica*, 23(3):269-271 (1973).

*Primary Examiner*—Ronald W. Griffin
*Assistant Examiner*—Nancy S. Carson
*Attorney, Agent, or Firm*—Sterne, Kessler, Goldstein & Fox

[57] ABSTRACT

Substantially pure saponins are disclosed. The saponins of the present invention are useful as immune adjuvants. Disclosed as well are immune response-provoking compositions comprising an antigen in admixture with the substantially pure saponins.

16 Claims, 23 Drawing Sheets

SAPONIN ADJUVANT

CROSS REFERENCE TO RELATED APPLICATIONS

This application is a continuation of application Ser. No. 07/200,754, filed 05/31/88 which is a continuation-in-part of U.S. patent application Ser. No. 055,229 filed May 29, 1987 and having the title "Saponin Adjuvant" both now abandoned.

This application is also related to U.S. patent application Ser. No. 55,298, which is a continuation-in-part of U.S. patent application Ser. No. 868,585, entitled "Method of Preparation and Use For Feline Leukemia Virus Antigens," in the names of Beltz et al.

BACKGROUND OF THE INVENTION

1. Field of the Invention

The present invention relates to the field of immune adjuvants, the process for production thereof, and the use thereof as immune adjuvants and vaccines.

2. Brief Description of the Background Art

Quillaja saponins are a mixture of triterpene glycosides extracted from the bark of the tree *Quillaja saponaria*. Crude saponins have been extensively employed as adjuvants in vaccines against foot and mouth disease, and in amplifying the protective immunity conferred by experimental vaccines against protozoal parasites such as *Trypanosoma cruzi* plasmodium and also the humoral response to sheep red blood cells (SRBC). (Bomford, *Int. Arch. Allerg. appl. Immun.*, 67:127 (1982)).

Saponins are natural products which have been characterized by a number of common properties. The ability to produce foam in aqueous solution gave the name to the group. Further characteristics are the hemolytic activity, the toxicity for fish, the complexing with cholesterol, and in some cases antibiotic activity. Kofler, *Die Saponine* (Springer Berlag), Berlin, 1927; Tschesche et al., *Chemine und Biologic der Saponine. Fortscher. Chem. Oro. Naturst.* XXX:461 (1972).

The common properties of saponins are not reflected in a common chemical composition. Although all saponins are glycosides, the aglycone may belong to the steroids, the triterpenoids, or the steroidalcaloids. The number of sugar and sugar chains attached to the glycosidic bonds may vary greatly. Saponins have been produced commercially and have many uses. The commercially available Quillaja saponins are crude mixtures which, because of their variability, are not desirable for use in veterinary practice or in pharmaceutical compositions for man. Because of the variability and heterogeneity, each batch must be tested in animal experiments to determine adjuvant activity and toxicity. The impurities in the commercially available products may produce adverse reactions. In addition, the content of the active substance in a given batch of saponin may vary, thereby decreasing the reproducibility from batch to batch.

An early attempt to purify Quillaja saponin adjuvants was made by Dalsgaard, *Archiv fuer die gesamte Virusforschung* 44:243 (1974). Dalsgaard partially purified an aqueous extract of the saponin adjuvant material from *Quillaja saponaria Molina*. Dalsgaard's preparation, commercially available from Superfos under the name "Quil-A," has been isolated from the bark of the South American tree, *Quillaja saponaria Molina*, and is characterized chemically as a carbohydrate moiety in glycosidic linkage to the triterpenoid quillaic acid. However, while the saponin Quil A of Dalsgaard presents a definite improvement over the previously available commercial saponins, it also shows considerable heterogeneity.

Higuchi et al., *Phytochemistry* 26:229 (January, 1987) treated a crude Quillaja saponin mixture with alkaline hydrolysis in 6% $NH_4HCO_3$ in 50% methanol and generated two major desacylsaponins, termed DS-1 and DS-2. DS-1 was shown to contain glucuronic acid, galactose, xylose, fucose, rhamnose, apiose, and Quillajic acid, whereas DS-2 contained these same components plus an additional glucose. Byproducts of this deacylation produced multiple components including 3,5-dihydroxy-6-methyloctanoic acid, 3,5-dihydroxy-6-methyloctanic acid, 5-α-L-arabinofuranoside and 5-O-α-L-rhamnopyranosyl-(1->2)-α-L-arabinofuranoside (Higuchi et al., *Phytochemistry* 26:2357 (August, 1987).

SUMMARY OF THE INVENTION

Figure 1:
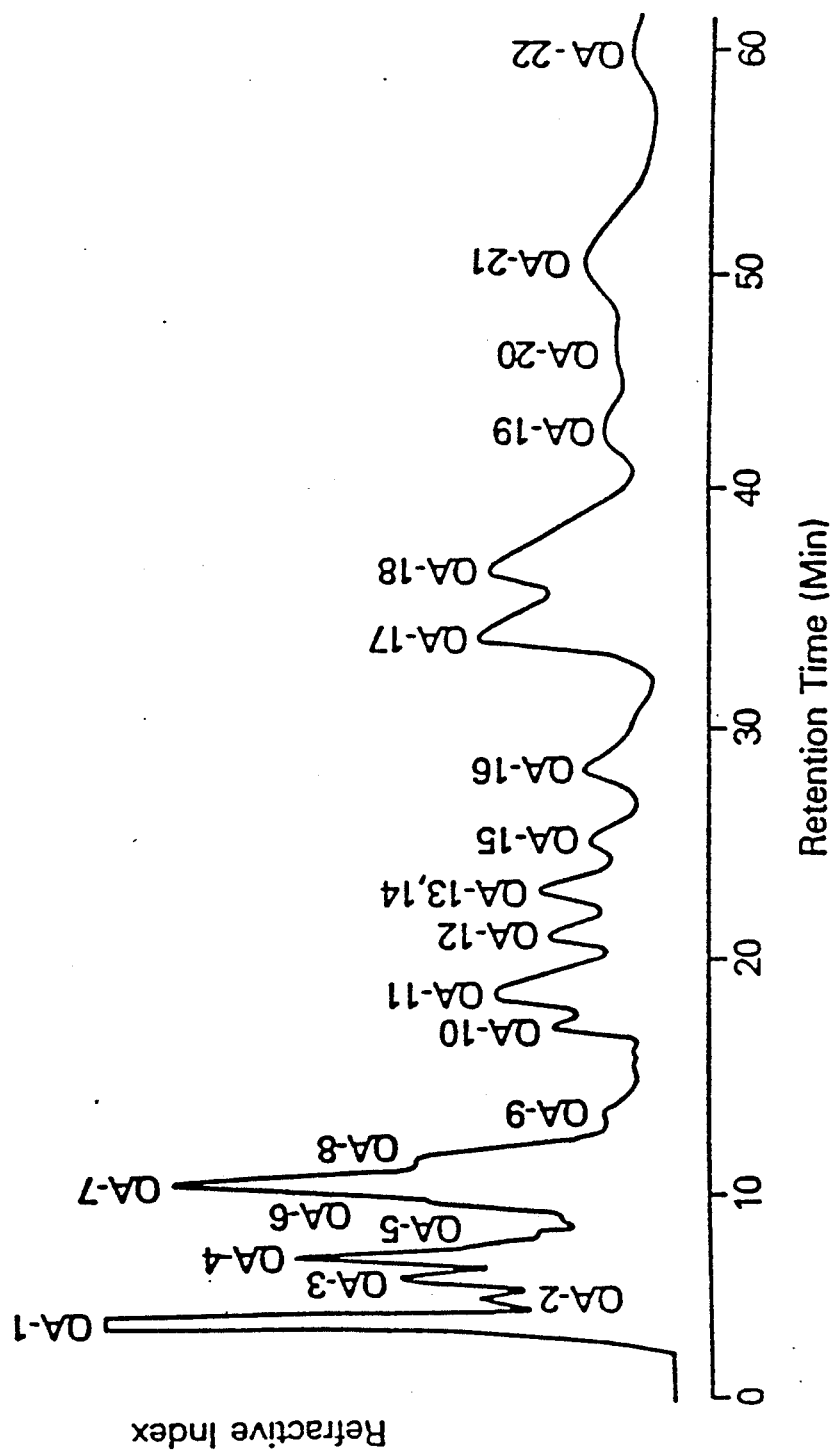
FIG. 1 shows the refractive index profile of dialyzed, methanol-solubilized Quillaja bark extract on reverse phase-HPLC.

A need exists for a substantially pure saponin that can be used as an adjuvant in relatively low quantities with low toxicity and side effects. Accordingly, the present invention provides substantially pure saponin adjuvants, the method for the purification thereof and a method for the use of the substantially pure saponins as immune adjuvants. The invention further includes immune response-provoking compositions comprising the saponin adjuvants in combination with an antigen component.

Adjuvant saponins have been identified and purified from an aqueous extract of the bark of the South American tree, Quillaja saponaria Molina. At least 22 peaks with saponin activity were separable. The predominant purified Quillaja saponins have been identified as QA-7, QA-17, QA-18, and QA-21. These saponins have been purified by high pressure liquid chromatography (HPLC) and low pressure silica chromatography. These four saponins have adjuvant effect in mice. QA-7, QA-17, QA-18, and QA-21, purified from Superfos "Quil-A," a crude Quillaja saponin preparation, are less toxic in mice than "Quil-A"; QA-17 and QA-18 are less toxic in cats than "Quil-A" (QA-7, QA-21 were not tested). In addition, a toxic component of Superfos "Quil-A" has been identified as QA-19; this component is toxic in mice at lower doses than "Quil-A" or QA-7, QA-17, QA-18, and QA-21. The increased toxicity of QA-19 compared to QA-7, QA-17, QA-18, and QA-21 is unexpected in that this component is a saponin, has a similar carbohydrate composition, exhibits adjuvant activity in mice at doses lower than the toxic dose, and exhibits similar chromatographic behavior. All of the above saponins may be isolated from aqueous extracts of Quillaja saponaria Molina bark. The substantially pure saponins of the present invention are useful as immune adjuvants and enhance immune responses in individuals at a much lower concentration than the previously available heterogeneous saponin preparations without the toxic effects associated with crude saponin preparations.

DESCRIPTION OF THE PREFERRED EMBODIMENTS

The saponins of the present invention may be obtained from the tree Quillaja saponaria Molina.

The term "saponin" as used herein includes glycosidic triterpenoid compounds which produce foam in aqueous solution, have hemolytic activity in most cases, and possess immune adjuvant activity. The invention encompasses the saponin per se, as well as natural and pharmaceutically acceptable salts and pharmaceutically acceptable derivatives. The term "saponin" also encompasses biologically active fragments thereof.

The invention also concerns compositions, such as immunologic compositions, comprising one or more substantially pure saponin fractions, and methods of using these compositions as immune adjuvants.

The term "immune adjuvant," as used herein, refers to compounds which, when administered to an individual or tested in vitro, increase the immune response to an antigen in the individual or test system to which said antigen is administered. Some antigens are weakly immunogenic when administered alone or are toxic to the individual at concentrations which evoke immune responses in said individual. An immune adjuvant may enhance the immune response of the individual to the antigen by making the antigen more strongly immunogenic. The adjuvant effect may also lower the dose of said antigen necessary to achieve an immune response in said individual.

The adjuvant activity of the saponins may be determined by any of a number of methods known to those of ordinary skill in the art. The increase in titer of antibody against specific antigen upon administration of an adjuvant may be used as a criteria for adjuvant activity (Dalsgaard, K. (1978) Acta Veterinia Scandinavica 69, 1-40, Scott, M. T., Gross-Samson, M., and Bomford, R. (1985) Int. Archs. Allergy Appl. Immun. 77, 409-412). Briefly, one such test involves injecting CD-1 mice intradermally with an antigen (for instance, i.e., bovine serum albumin, BSA) mixed with varying amounts of the potential adjuvant. Sera was harvested from the mice two weeks later and tested by ELISA for anti-BSA antibody. A comparison of the adjuvant effects of the dialyzed, methanolsoluble bark extract and "Quil A" showed that antibody titers were two orders of magnitude greater when the antigen BSA was administered in the presence of the saponin preparations than when BSA was administered in PBS alone. The bark extract possessed good adjuvant activity when administered at an adjuvant dose of 12 $\mu$g carbohydrate (assayed by anthrone) or more. The adjuvant response to "Quil-A" was lower than for the bark extract but was evident at doses ranging from 9-23 $\mu$g carbohydrate. Carbohydrate weight (determined by assay with anthrone using glucose as a standard) is approximately 30% of the dry weight of these crude adjuvant extracts.

The term "substantially pure" means substantially free from compounds normally associated with the saponin in its natural state and exhibiting constant and reproducible chromatographic response, elution profiles, and biologic activity. The term "substantially pure" is not meant to exclude artificial or synthetic mixtures of the saponin with other compounds.

Preferably, the substantially pure saponin is purified to one or more of the following standards: 1) appearing as only one major carbohydrate staining band on silica gel TLC (EM Science HPTLC Si60) in a solvent system of 40 mM acetic acid in chloroform/methanol/water (60/45/10, v/v/v), 2) appearing as only one major carbohydrate staining band on reverse phase TLC (EM Science Silica Gel RP-8) in a solvent system of methanol/water (70/30, v/v), 3) appearing as only one major peak upon reverse-phase HPLC on Vydac C4 (5 $\mu$m particle size, 330 Å pore, 4.6 mm ID×25 cm L) in 40 mM acetic acid in methanol/water (58/42, v/v).

Figure 2:
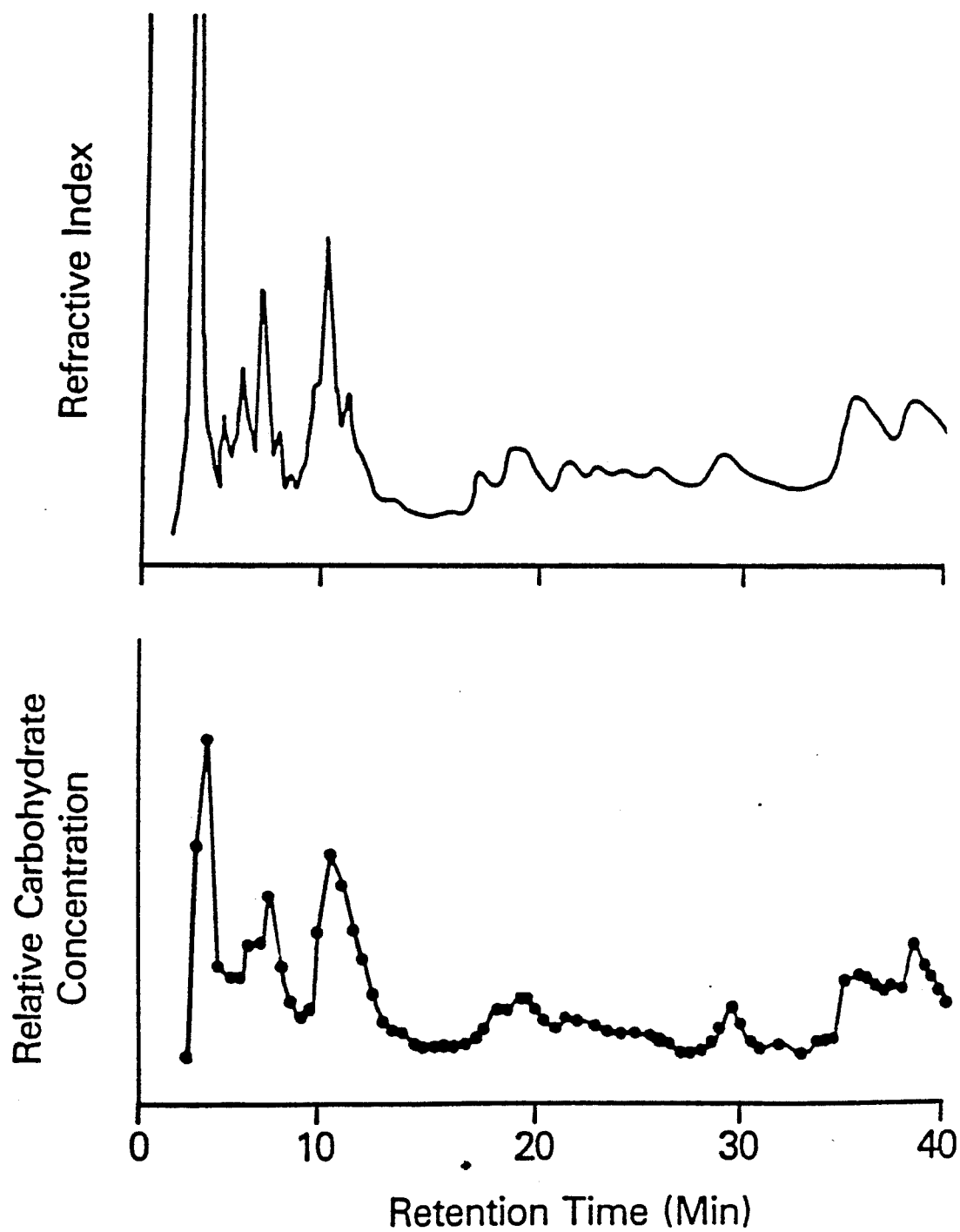
FIG. 2 shows that the refractive index peaks of the above sample correspond to carbohydrate peaks.

In the preferred embodiment, the saponin adjuvants of the present invention are purified from Quillaja saponaria Molina bark. Aqueous extracts of the Quillaja saponaria Molina bark were dialyzed against water. The dialyzed extract was lyophilized to dryness, extracted with methanol and the methanol-soluble extract was further fractionated on silica gel chromatography and by reverse phase high pressure liquid chromatography (RP-HPLC). The individual saponins were separated by reverse phase HPLC as described in Example 1. At least 22 peaks (denominated QA-1 to QA-22) were separable. Each peak corresponded to a carbohydrate peak as demonstrated in FIG. 2 and exhibited only a single band on reverse phase thin layer chromatography. The individual components were identified by retention time on a Vydac C₄ HPLC column as follows:

| Peak | Retention Time (minutes) |
| --- | --- |
| QA-1 | solvent front |
| QA-2 | 4.6 |
| QA-3 | 5.6 |
| QA-4 | 6.4 |
| QA-5 | 7.2 |
| QA-6 | 9.2 |
| QA-7 | 9.6 |
| QA-8 | 10.6 |
| QA-9 | 13.0 |
| QA-10 | 17.2 |
| QA-11 | 19.0 |
| QA-12 | 21.2 |
| QA-13 | 22.6 |
| QA-14 | 24.0 |
| QA-15 | 25.6 |
| QA-16 | 28.6 |
| QA-17 | 35.2 |
| QA-18 | 38.2 |
| QA-19 | 43.6 |
| QA-20 | 47.6 |
| QA-21 | 51.6 |
| QA-22 | 61.0 |

Immune adjuvant activity was tested by measuring the ability of the purified saponins to enhance the immune response in mice to exogenously administered antigens. The purified saponins of the present invention demonstrated adjuvant effects at lower doses than the crude extracts. Particularly, the predominant saponins in bark extract (QA-7, QA-17, QA-18, and QA-21) demonstrated adjuvant activity at doses of 4.5 µg carbohydrate or less (assayed by anthrone). The purified saponins were further characterized by carbohydrate content, reverse phase and normal phase TLC, UV, infra red, NMR spectra, and fast atom bombardment—mass spectroscopy.

The approximate extinction coefficient determined for 1% (w/v) solutions in methanol at 205 nm of several of the more preferred purified saponins are as follows:

|  | 1% $E_{205}$ (nm) |
| --- | --- |
| QA-7 | 34 |
| QA-17 | 27 |
| QA-18 | 27 |
| QA-21 | 28 |

Carbohydrate content was used to quantitate the saponins in some instances. The carbohydrate assay was the anthrone method of Scott and Melvin (*Anal. Chem.* 25:1656 (1953)) using glucose as a standard as described in Example 1. This assay was used to determine a ratio of extent of anthrone reaction (expressed in glucose equivalents) per mg of purified saponin (dry weight) so that dry weight of a particular preparation could be estimated by use of anthrone assay. It must be noted that differences in reactivity with anthrone for different saponins may be due to carbohydrate composition rather than quantity as different monosaccharides react variably in this assay.

The substantially pure QA-7 saponin is characterized as having immune adjuvant activity, containing about 35% carbohydrate (as assayed by anthrone) per dry weight, having a uv absorption maxima of 205-210 nm, a retention time of approximately 9-10 minutes on RP-HPLC on a Vydac C₄ column having 5 µm particle size, 330 Å pore, 4.6 mm ID×25 cm L in a solvent of 40 mM acetic acid in methanol/water (58/42; v/v) at a flow rate of 1 ml/min, eluting with 52-53% methanol from a Vydac C₄ column having 5 µm particle size, 330 Å pore, 10 mM ID×25 cm L in a solvent of 40 mM acetic acid with gradient elution from 50 to 80% methanol, having a critical micellar concentration of approximately 0.06% in water and 0.07% in phosphate buffered saline, causing no detectable hemolysis of sheep red blood cells at concentrations of 200 µg/ml or less, and containing the monosaccharide residues terminal rhamnose, terminal xylose, terminal glucose, terminal galactose, 3-xylose, 3,4-rhamnose, 2,3-fucose, and 2,3-glucuronic acid, and apiose (linkage not determined).

The substantially pure QA-17 saponin is characterized as having adjuvant activity, containing about 29% carbohydrate (as assayed by anthrone) per dry weight, having a UV absorption maxima of 205-210 nm, a retention time of approximately 35 minutes on RP-HPLC on a Vydac C₄ column having 5 µm particle size, 330 Å pore, 4.6 mm ID×25 cm L in a solvent of 40 mM acetic acid in methanol-water (58/42; v/v) at a flow rate of 1 ml/min, eluting with 63-64% methanol from a Vydac C₄ column having 5 µm particle size, 330 Å pore, 10 mm ID×25 cm L in a solvent of 40 mM acetic acid with gradient elution from 50 to 80% methanol, having a critical micellar concentration of 0.06% (w/v) in water and 0.03% (w/v) in phosphate buffered saline, causing hemolysis of sheep red blood cells at 25 µg/ml or greater, and containing the monosaccharide residues terminal rhamnose, terminal xylose, 2-fucose, 3-xylose, 3,4-rhamnose, 2,3-glucuronic acid, terminal glucose, 2-arabinose, terminal galactose and apiose (linkage not determined).

The substantially pure QA-18 saponin is characterized as having immune adjuvant activity, containing about 25-26% carbohydrate (as assayed by anthrone) per dry weight, having a UV absorption maxima of 205-210 nm, a retention time of approximately 38 minutes on RP-HPLC on a Vydac C₄ column having 5 µm particle size, 330 Å pore, 4.6 mm ID×25 cm L in a solvent of 40 mM acetic acid in methanol/water (58/42; v/v) at a flow rate of 1 ml/min, eluting with 64-65% methanol from a Vydac C₄ column having 5 µm particle size, 330 Å pore, 10 mm ID×25 cm L in a solvent of 40 mM acetic acid with gradient elution from 50 to 80% methanol, having a critical micellar concentration of 0.04% (w/v) in water and 0.02% (w/v) in phosphate buffered saline, causing hemolysis of sheep red blood cells at concentrations of 25 µg/ml or greater, and containing the monosaccharides terminal rhamnose, terminal arabinose, terminal apiose, terminal xylose, terminal glucose, terminal galactose, 2-fucose, 3-xylose, 3,4-rhamnose, and 2,3-glucuronic acid.

The substantially pure QA-21 saponin is characterized as having immune adjuvant activity, containing about 22% carbohydrate (as assayed by anthrone) per dry weight, having a UV absorption maxima of 205-210 nm, a retention time of approximately 51 minutes on RP-HPLC on a Vydac C₄ column having 5 µm particle size, 330 Å pore, 4.6 mm ID×25 cm L in a solvent of 40 mM acetic acid in methanol/water (58/42; v/v) at a flow rate of 1 ml/min, eluting with 69 to 70% methanol from a Vydac C₄ column having 5 µm particle size, 330 Å pore, 10 mm×ID 25 cm L in a solvent of 40 mM acetic acid with gradient elution from 50 to 80% methanol, with a critical micellar concentration of about 0.03% (w/v) in water and 0.02% (w/v) in phosphate buffered saline, causing hemolysis of sheep red blood cells at concentrations of 25 μg/ml or greater, and containing the monosaccharides terminal rhamnose, terminal arabinose, terminal apiose, terminal xylose, 4-rhamnose, terminal glucose, terminal galactose, 2-fucose, 3-xylose, 3,4-rhamnose, and 2,3-glucuronic acid.

The term "individual" means any animal which can elicit an immune response, including humans.

The purified saponins exhibit adjuvant effects when administered over a wide range of dosages and a wide range of ratios to the antigen being administered. In one embodiment, the saponin is administered in a ratio of adjuvant to antigen (w/w) of 3.0 or less, preferably 1.0 or less.

The purified saponins may be administered either individually or admixed with other substantially pure adjuvants to achieve the enhancement of the immune response to an antigen. Among the adjuvant mixtures effective in the present invention are fractions QA-7 and QA-17, QA-7 and QA-18, QA-17 and QA-18, or QA-7, QA-17, and QA-18 administered together. Purified saponins may also be administered together with non-saponin adjuvants. Such non-saponin adjuvants useful with the present invention are oil adjuvants (for example, Freund's Complete and Incomplete), liposomes, mineral salts (for example, $AlK(SO_4)_2$, $AlNa(SO_4)_2$, $AlNH_4(SO_4)$, silica, alum, $Al(OH)_3$, $Ca_3(PO_4)_2$, kaolin, and carbon), polynucleotides (for example, poly IC and poly AU acids), and certain natural substances (for example, wax D from *Mycobacterium tuberculosis*, as well as substances found in *Corynebacterium parvum*, *Bordetella pertussis*, and members of the genus Brucella).

The purified saponins of the present invention may be utilized to enhance the immune response to any antigen. Typical antigens suitable for the immune-response provoking compositions of the present invention include antigens derived from any of the following: viruses, such as influenza, rabies, measles, hepatitis B, hoof and mouth disease, or HTLV-III; bacteria, such as anthrax, diphtheria or tuberculosis; or protozoans, such as *Babeosis bovis* or Plasmodium.

A particular example is the use of the purified saponins of the present invention to enhance the immune response to gp70 recombinant protein. One gp70 recombinant protein is an antigen which contains the polypeptide portion of FeLV gp70 envelope protein. This recombinant antigen is termed "gp70R," "rec-gp70" or "Rgp70." Another antigen preparation which contains the polypeptide portion of FeLV gp70 together with the 40 amino-terminal amino acids (termed "Rgp70delta") or with the entire amino acid sequence (termed "Rgp90") of the p15e envelope protein of FeLV subgroup A is produced using recombinant DNA techniques. These recombinant gp70-containing polypeptides, gp70R, gp70R-delta, and gp90R, are hereinafter referred to collectively as gp70-containing protein. The term gp70-containing protein is intended to include polypeptides having the same amino acid sequence of the naturally occurring gp70-containing protein, and analogs thereof. The term "analogs" is intended to include proteins or polypeptides which differ from gp70, gp70-delta, or gp90 by addition, deletion or substitution of one or more amino acids providing that said polypeptide demonstrate substantially the biological activity of gp70 protein.

Administration of the compounds useful in the method of present invention may be by parenteral, intravenous, intramuscular, subcutaneous, intranasal, or any other suitable means. The dosage administered may be dependent upon the age, weight, kind of concurrent treatment, if any, and nature of the antigen administered. The effective compound useful in the method of the present invention may be employed in such forms as capsules, liquid solutions, suspensions or elixirs for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

Having now generally described the invention, the same may be further understood by reference to the following examples, which are not intended to be limiting unless so expressly stated.

EXAMPLE 1

Preliminary Preparation of *Quillaja Saponaria Molina* Bark Extract

*Quillaja saponaria Molina* bark was stirred with an excess of water (10% w/v) to extract the saponins. The aqueous extract was then filtered and stored in 0.1% $NaN_3$. 150 ml of this extract was centrifuged at 20,000×g for 30 minutes to remove residual bark fragments. The supernatant, which was light brown, was lyophilized and redissolved in 16 ml of water and the pH was adjusted to less than 4 with the addition of 160 μl of 1N acetic acid. This solution was placed in dialysis tubing having a 12,000 MW cut off and dialyzed against 1 liter of water. The water was changed after 8 hours of dialysis, and the dialysis was allowed to proceed overnight. Samples of the dialysate were removed after the first and second dialysis cycles. The dialyzed extract was lyophilized and extracted with 40 ml methanol at 60° C. for 15 minutes followed by centrifugation at 1,000×g for 10 minutes to sediment the undissolved material. This material was subjected to two additional extractions with methanol. The methanol extracts were pooled, evaporated on a rotoevaporator to dryness, redissolved in 5.5 ml methanol, and filtered through a 0.2μ nylon 66 mesh to remove residual undissolved material. Fractions were analyzed by reverse phase thin-layer chromatography (RP-TLC) on C8 plates (E.M. Science RP-TLC, C8) in a solvent system of 70% methanol/30% water or by normal phase thin layer chromatography on silica gel 60 TLC plates in a solvent system of n-butanol, ethanol, water, and ammonia (30/60/29/21, v/v/v/v). The carbohydrate bands were visualized with Bial's reagent which detected all major bands detectable by sulfuric acid charring with an increased sensitivity over the sulfuric acid charring method. The Bial's reagent carbohydrate stain was routinely used as a detection reagent on TLC plates. All major bands were glycosylated.

Dialysis removed a major carbohydrate-containing band ($R_F$=0.82 on EM Science RP TLC, C8 in methanol/water (70/30, v/v)), as well as some minor components. In addition, dialysis removed components with strong absorption maxima at 280 and 310 nm. Approximately 80% of the carbohydrate (assayed by anthrone) was removed by dialysis, but about 95% of the hemolytic activity was retained during dialysis.

Most saponin adjuvants are known to have detergent properties, such as hemolysis of red blood cells, so the retention of hemolytic activity is a rough indication of the retention of adjuvant saponins. Several bands were retained by dialysis, indicating their detergent nature.

Methanol solubilized all TLC bands present in the dialyzed extract except one TLC band ($R_F=0$ on both reverse-phase and silica TLC plates). The methanol-insoluble material was reddish-brown. The material which was methanol-soluble appeared white after lyophilization.

Carbohydrate concentration was determined by the method of Scott and Melvin (Scott, T. A., and Melvin, E. H. *Anal. Chem.* 25, 1656 (1953)). Briefly, an aqueous sample to be tested or glucose as a standard carbohydrate solution (450 μl) was mixed with 900 μl of 0.2% anthrone (w/v) in sulfuric acid and incubated for 16 min at 90°–100° C. The absorbance was read at 625 nm. Glucose was used as a standard.

The hemolytic activity of the samples was determined as follows: Briefly, samples were diluted in a round bottom microtiter plate with 1:2 dilutions in phosphate buffered saline in successive rows (100 μl/well). 10 μl normal rabbit blood in Alsevers solution (Hazelton) was added to each well and mixed. Plates were incubated for one hour at room temperature followed by centrifugation of the plates in a Sorvall RT6000 to sediment unhemolyzed cells. Absence of hemolysis was determined by the presence of a pellet of unhemolyzed cells in the bottom of the well.

EXAMPLE 2

Comparison of Dialyzed, Methanol-Soluble Bark Extract and Superfos "Quil-A" by TLC and HPLC Superfos "Quil-A" and dialyzed, methanolsoluble components of bark extract prepared as in Example 1 were compared by reverse phase TLC as described in Example 1. All bands present in the bark extract after dialysis and solubilization with methanol were present in "Quil-A." In addition, "Quil-A" contained a band with $r_f=0$ on reverse-phase TLC plates; this component was removed by methanol-solubilization as described above. The similarity in composition of dialyzed, methanolsoluble bark extract and "Quil-A" was confirmed by HPLC. The individual components of bark extract were separable by reverse-phase HPLC on Vydac C4 (5 μm particle size, 330 Å pore, 4.6 mm ID×25 cm L) in 40 mM acetic acid in methanol/water (58/42, v/v). The refractive index of the individual fractions was determined. FIG. 1 represents the refractive index profile of the peaks (labeled QA-1 to QA-22 in order of increasing retention times) from the RP-HPLC. The relative proportion of each peak in bark extract and Superfos "Quil-A" is shown on Table 1, below.

TABLE 1

Relative proportion of HPLC fractions of crude saponin extract and Superfos "Quil-A" (refractive index) % of Total (peaks 2–21)

| HPLC Fraction | Dialyzed, methanol-soluble bark extract | Superfos "Quil-A" |
| --- | --- | --- |
| QA-2 | 3.1 | 1.2 |
| QA-3 | 4.8 | 2.4 |
| QA-4,5 | 10.1 | 7.1 |
| QA-6,7 | 17.5 | 12.7 |
| QA-8 | 6.8 | 10.5 |
| QA-9 | 1.0 | 2.1 |
| QA-10 | 2.7 | 1.3 |
| QA-11 | 6.8 | 6.2 |
| QA-12 | 3.5 | 5.6 |
| QA-13,14,15 | 4.8 | 7.7 |
| QA-16 | 2.8 | 1.4 |
| QA-17 | 11.4 | 9.9 |

TABLE 1-continued

Relative proportion of HPLC fractions of crude saponin extract and Superfos "Quil-A" (refractive index) % of Total (peaks 2–21)

| HPLC Fraction | Dialyzed, methanol-soluble bark extract | Superfos "Quil-A" |
| --- | --- | --- |
| QA-18 | 13.5 | 21.8 |
| QA-19 | 2.2 | 4.5 |
| QA-20 | 3.2 | 2.2 |
| QA-21 | 5.6 | 3.7 |

The individual peaks correspond to single thin-layer chromatography bands on reverse-phase TLC plates. Another representative experiment shown on FIG. 2 demonstrates that the refractive index peaks also correspond to carbohydrate peaks, confirming that all major bark extract components are glycosides (HPLC fractions assayed for carbohydrate by the anthrone assay).

Figure 3:
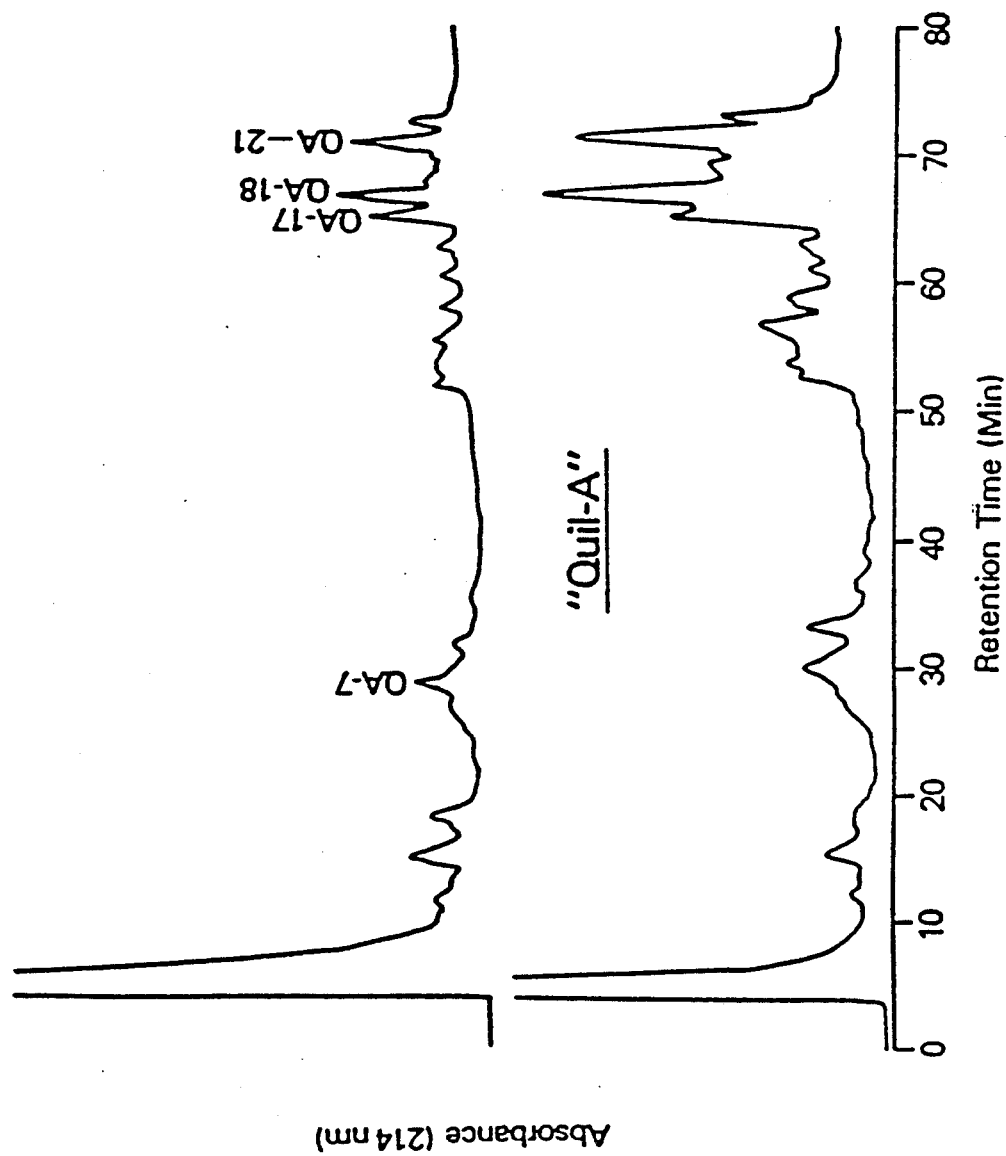
FIG. 3 shows the comparison of Superfos "Quil-A" and dialyzed methanol soluble bark extract by HPLC.

Dialyzed, methanol-soluble bark extract and "Quil-A" were compared directly in this HPLC system. The individual components were identified by retention time. All peaks present in dialyzed, methanol-soluble bark extract were also present in "Quil-A" in similar proportions with the exception of a higher proportion of component QA-8 and a lower proportion of component QA-17 in Superfos "Quil-A" compared to bark extract. FIG. 3 shows a comparison of dialyzed, methanol-soluble bark extract and Superfos "Quil-A" using a semipreparative Vydac C4 (10 mm ID×25 cm L, 330 Å pore size, 5 μm particle size). The sample is loaded in 50% methanol in 40 nM acetic acid and a methanol gradient in 40 mM acetic acid (shown in FIG. 3) is used to elute the samples. The absorbance was monitored at 214 nm.

Various samples of Quillaja bark were extracted and analyzed by HPLC. There was some variability in the relative proportions of the peaks, but the same peaks were always present. It is not presently known whether the variability in proportions is due to variability in the efficiency of the extraction process or in bark from different sources.

Due to the ready availability of "Quil-A" and the similar composition to bark extract, "Quil-A" was utilized to produce mg quantities of material. Adjuvant activity in mice, using BSA as antigen, was found to be associated with peaks 4, 7, 11, 12, 15, 16, 17, 18, 19, and 20 (Table 2) at doses of 3.0 μg carbohydrate (determined by the anthrone assay). The absorbance due to antigen-specific antibody binding (two weeks post-immunization, determined by ELISA) at a sera dilution of 1:10 provides a semi-quantitative estimate of adjuvant activity (ranging from 0.07 in mice immunized in the absence of adjuvant to 1.24 in mice immunized in the presence of QA-20).

TABLE 2

Adjuvant Activity in Mice

| HPLC Fraction | Adjuvant Dose (μg carbohydrate) | Absorbance* (410 nm) |
| --- | --- | --- |
| QA-2 | 3.0 | .34 |
| QA-3 | 3.0 | .27 |
| QA-4 | 3.0 | .60 |
| QA-7 | 3.0 | .49 |
| QA-10 | 3.0 | .13 |
| QA-11 | 3.0 | .46 |
| QA-12 | 3.0 | .76 |
| QA-13,14 | 3.0 | .20 |
| QA-15 | 3.0 | 1.17 |

TABLE 2-continued

| | Adjuvant Activity in Mice | |
|---|---|---|
| HPLC Fraction | Adjuvant Dose (μg carbohydrate) | Absorbance* (410 nm) |
| QA-16 | 3.0 | .66 |
| QA-17 | 3.0 | 1.13 |
| QA-18 | 3.0 | .75 |
| QA-19 | 3.0 | .93 |
| QA-20 | 3.0 | 1.24 |
| | | 0.07 |

*Absorbance due to antigen-specific antibody binding at sera dilution of 1:10.

Due to the predominance of peaks QA-7, QA-17, QA-18, and QA-21 in bark extract, these four components were purified on a layer scale, as described in Examples 3 and 4, below.

EXAMPLE 3

Purification by Silica Chromatograph 1 gram "Quil-A" was suspended in 75 ml methanol and heated at 60° for 15 minutes and filtered. The undissolved material was extracted a second time with 50 ml methanol at 60° C. and filtered. The filtrates were evaporated to dryness on the rotoevaporator. A Lichropep Silica Si60 column (E.M. Science, 25 mm ID×310 mm L, 40-63 μm particle size) was pre-equilibrated in 40 mM acetic acid in chloroform/methanol/water (62/32/6, v/v/v).

The dried "Quil-A," a crude mixture of saponins, was dissolved in 5 ml of column solvent and eluted through the silica isocratically in this solvent system at a flow rate of 1 ml/min. Carbohydrate analysis, thin-layer chromatography, and HPLC were used to monitor the fractions for QA-7, QA-17, QA-18, and QA-21. Fractions 19-30 were enriched in QA-21 and were pooled for further purification of QA-21. Fractions 31-60 were enriched in QA-8 and QA-18 and were pooled for further purification of these components. Fractions 85-104 were enriched with QA-7 and QA-17 and were pooled for further purification of these components. These pools were flash evaporated prior to further purification.

EXAMPLE 4

Further Purification by Reverse Phase HPLC

Silica fractions were further purified by semipreparative reverse phase HPLC on Vydac C4 (10 mm ID×25 cm L), FIG. 4. Silica fractions (10-20 mg) were dissolved in the appropriate solvent and loaded on Vydac C4. A methanol gradient was used to elute the fractions. The flow rate was 3 ml per minute. The fractions were monitored by absorbance at 214 nm. FIG. 4B shows the purification of QA-21 from silica fractions 19-30 using isocratic separation in 40 mM acetic acid in 58% methanol/42% water. Fractions eluting with a retention time between 65-72 minutes were identified as QA-21 by reverse phase TLC and pooled for further characterization. FIG. 4C shows the purification of QA-18 from silica fractions 31-60 using a methanol gradient in 40 mM acetic acid (50-56% methanol/0-10 min, 56-69% methanol/10-79 min). Fractions eluting with a retention time between 46-48 minutes were identified as QA-18 by reverse phase TLC and pooled for further characterization. FIG. 4D shows the purification of QA-7 and QA-17 from silica fractions 85-104 using the same gradient used in FIG. 4C. Fractions eluting with a retention time between 21-23 minutes were identified as QA-17 by reverse phase TLC and pooled for further characterization. Fractions eluting with a retention time between 44-46 minutes were identified as QA-17 by reverse phase TLC and were pooled for further characterization.

EXAMPLE 5

Figure 5A:
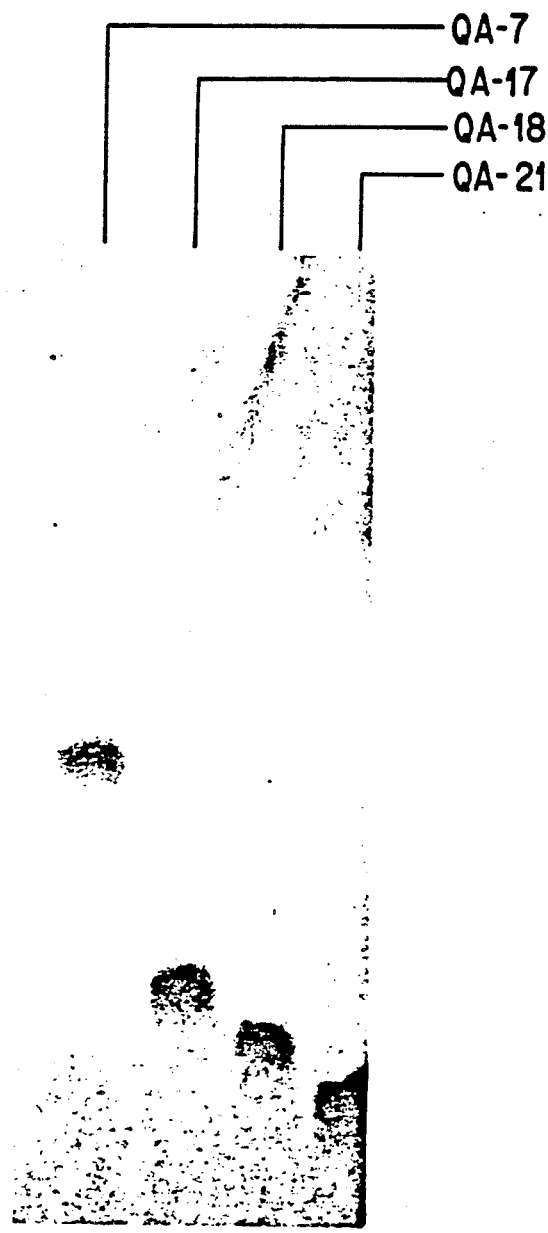
FIG. 5 demonstrates the purity of QA-7, QA-17, QA-18, and QA-21 by reverse phase (5A) and normal phase (5B) thin layer chromatography.

Purity and Characterization of Adjuvants Purified by Silica and Reverse Phase Chromatography Purity FIG. 5a represents a reverse-phase TLC (E.M. Science RP-TLC, C8 (Solvent=70% methanol, visualization spray=Bial's reagent)). 5 μg each of QA-7, QA-17, QA-18, and QA-21 purified as described in Example 3 and 4, were chromatographed. The adjuvants each appeared as single bands in this TLC system.

Figure 5B:
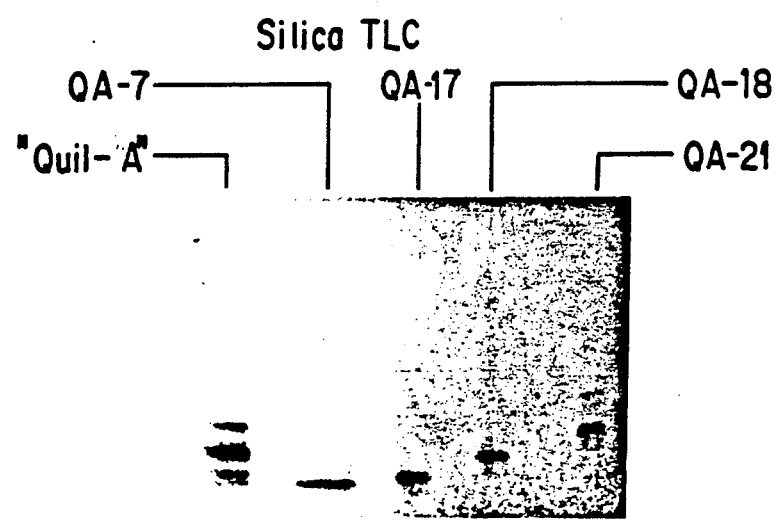
Figure 6:
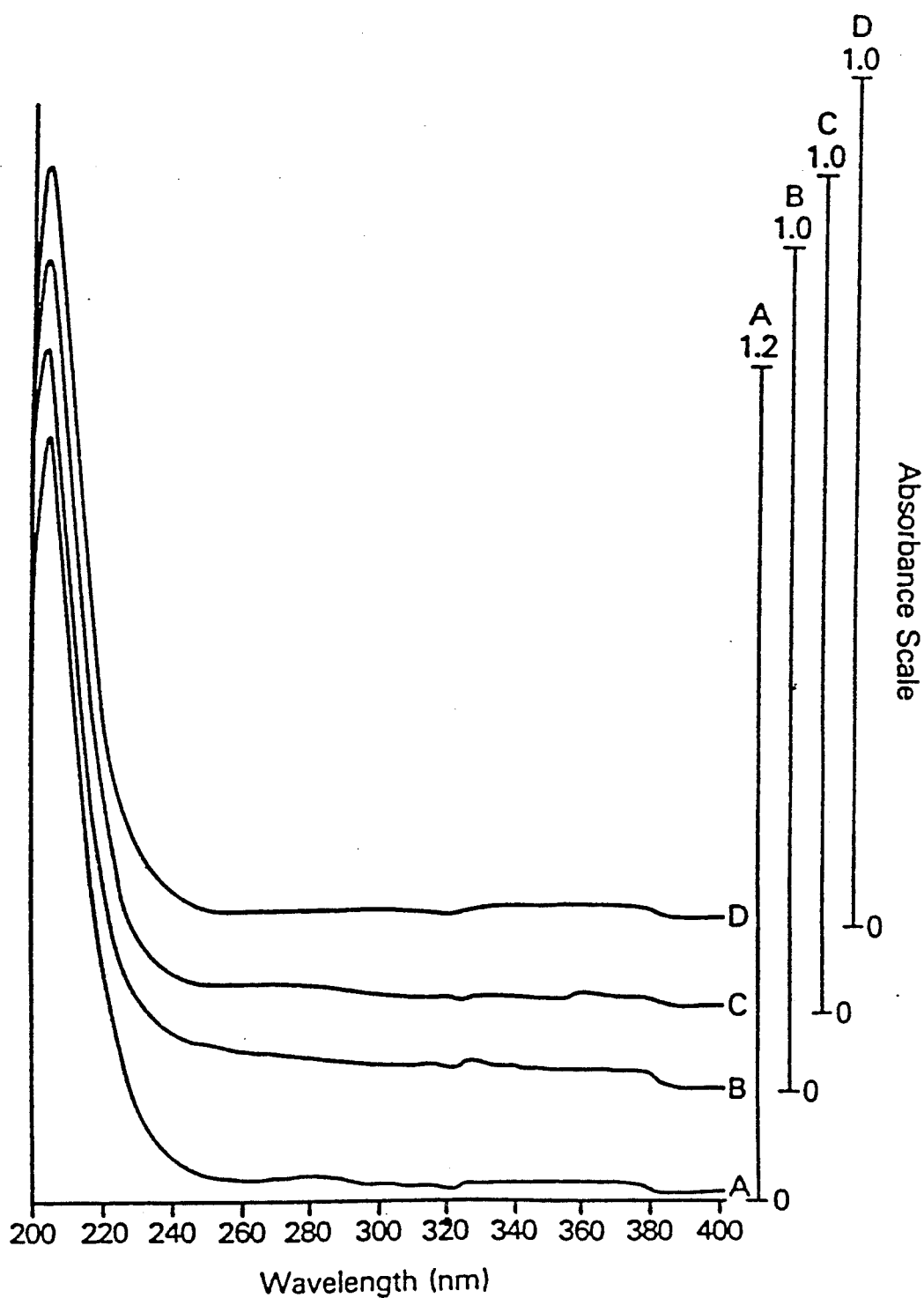
FIG. 6A shows the UV spectrum of QA-7.
FIG. 6B shows the UV spectrum of QA-17.
FIG. 6C shows the UV spectrum of QA-18.
FIG. 6D shows the UV spectrum of QA-21.

FIG. 5b demonstrates fractions QA-7, QA-17, QA-18, QA-21 and "Quil-A" on EM Si60 HPTLC plate (solvent=40 mM acetic acid in chloroform/methanol/$H_2O$ (60/45/10, v/v/v), visualization spray=Bial's reagent). 2 μg each of QA-7, QA-17, QA-18 and QA-21, purified as described in Examples 3 and 4, and 20 μg of "Quil-A," a crude saponin extract, were chromatographed. The HPLC-purified material appeared predominantly as a single band.

Spectroscopy

The UV spectra of QA-7, QA-17, QA-18 and QA-21 in methanol are shown on FIGS. 6A-D respectively. Dalsgaard's (Dalsgaard, K., *Acta Veterinaria Scandinavica Supp.* 69:1-40 (1978)) adjuvant fraction had an absorbance peak at 280 nm; however, the HPLC-purified fractions of the present invention do not have a peak at 280 nm but have a major peak in the region between 200-220 nm with a shoulder centered at 260 nm.

Fourier Transform-Infrared Resonance ("FT-IR") spectra showed little difference between the adjuvants, suggesting that they all have the same functional groups. Although identification of the structure cannot be made from the IR, the spectral data is consistent with the presence of a carboxyl group as was suggested by Dalsgaard (Dalsgaard, K., supra).

Figure 7A:
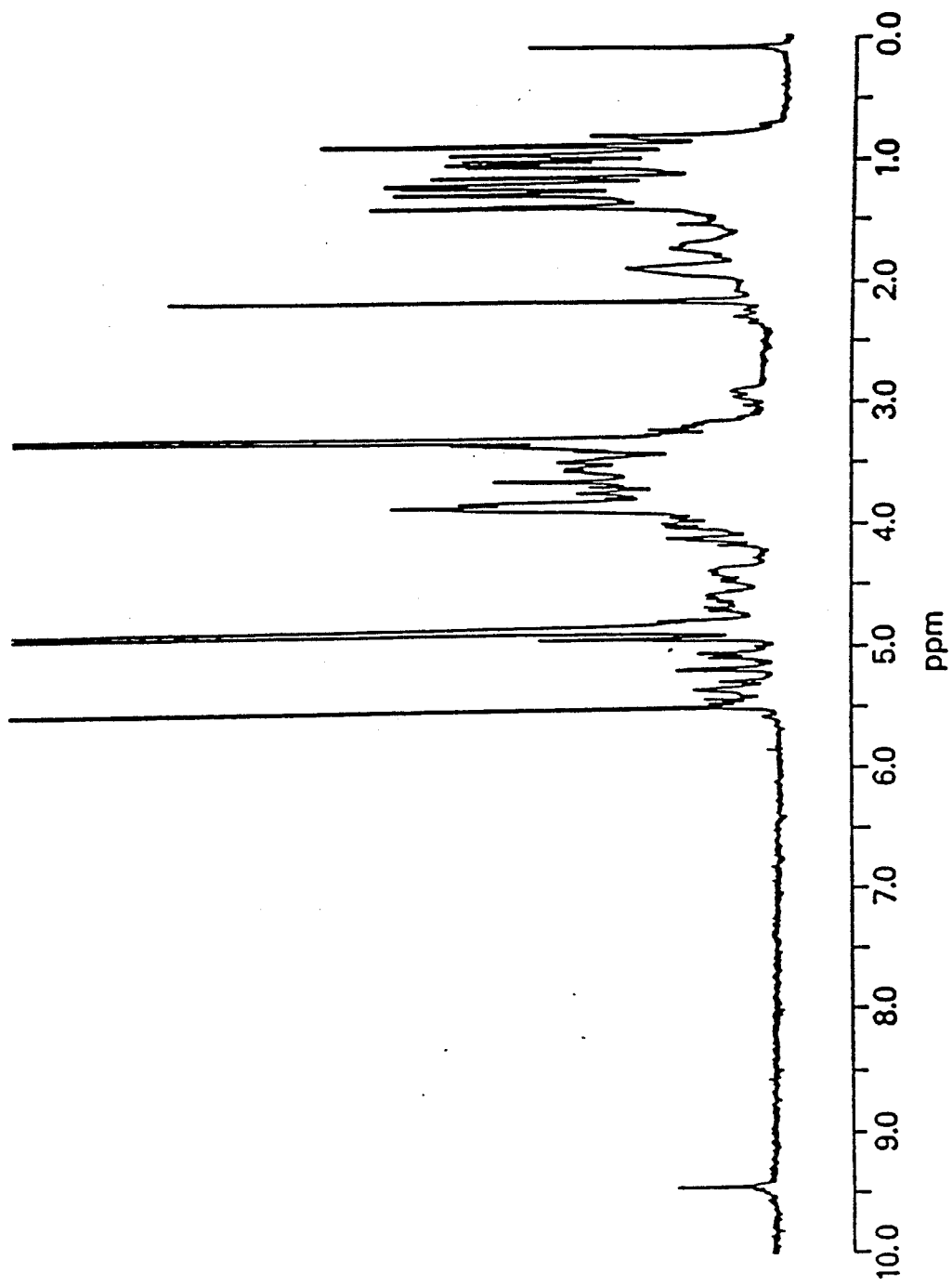
FIG. 7A shows 'H Nuclear Magnetic Resonance ("NMR") of QA-7.
Figure 7B:
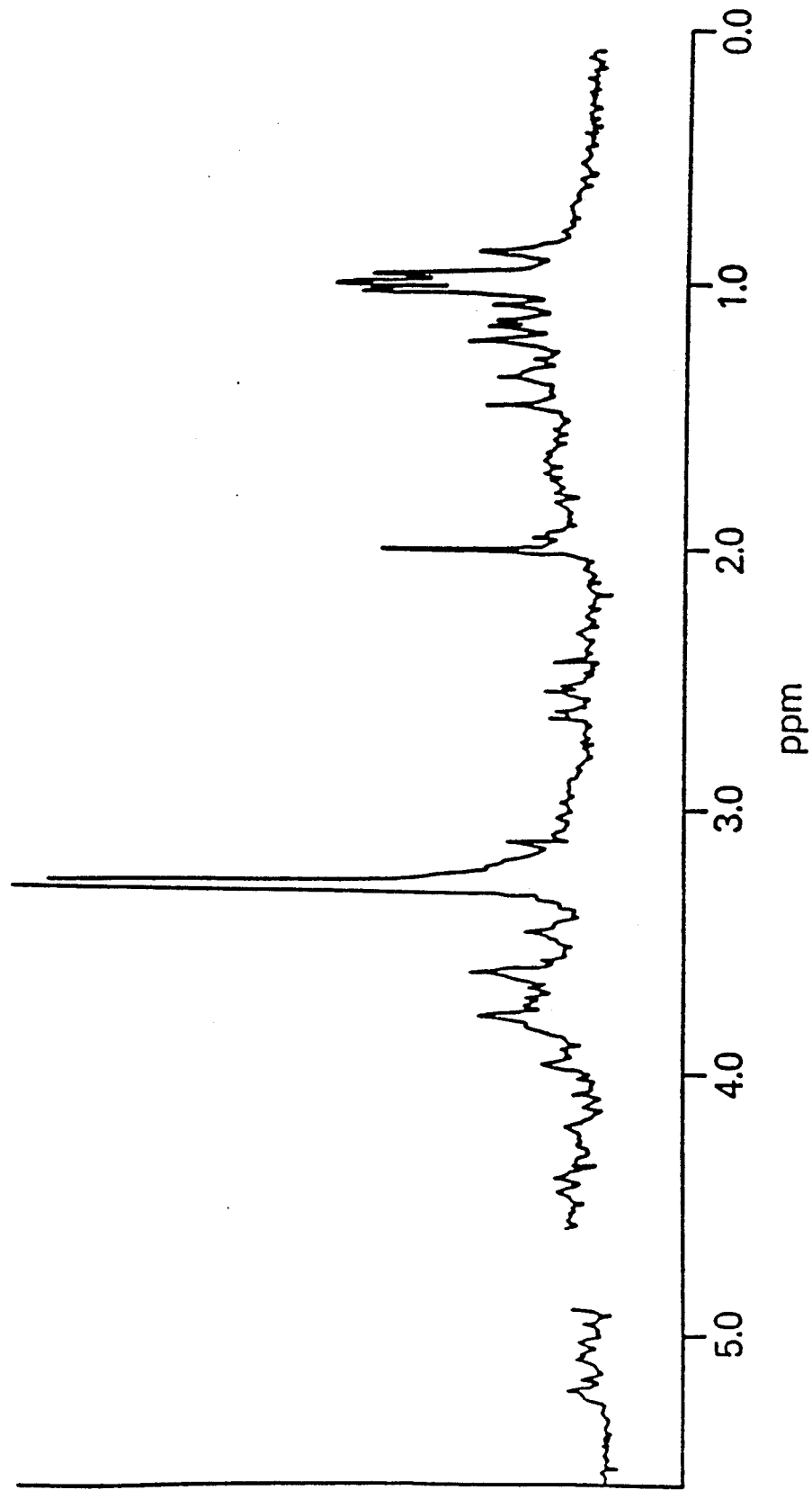
FIG. 7B shows 'H NMR of QA-18.
Figure 7C:
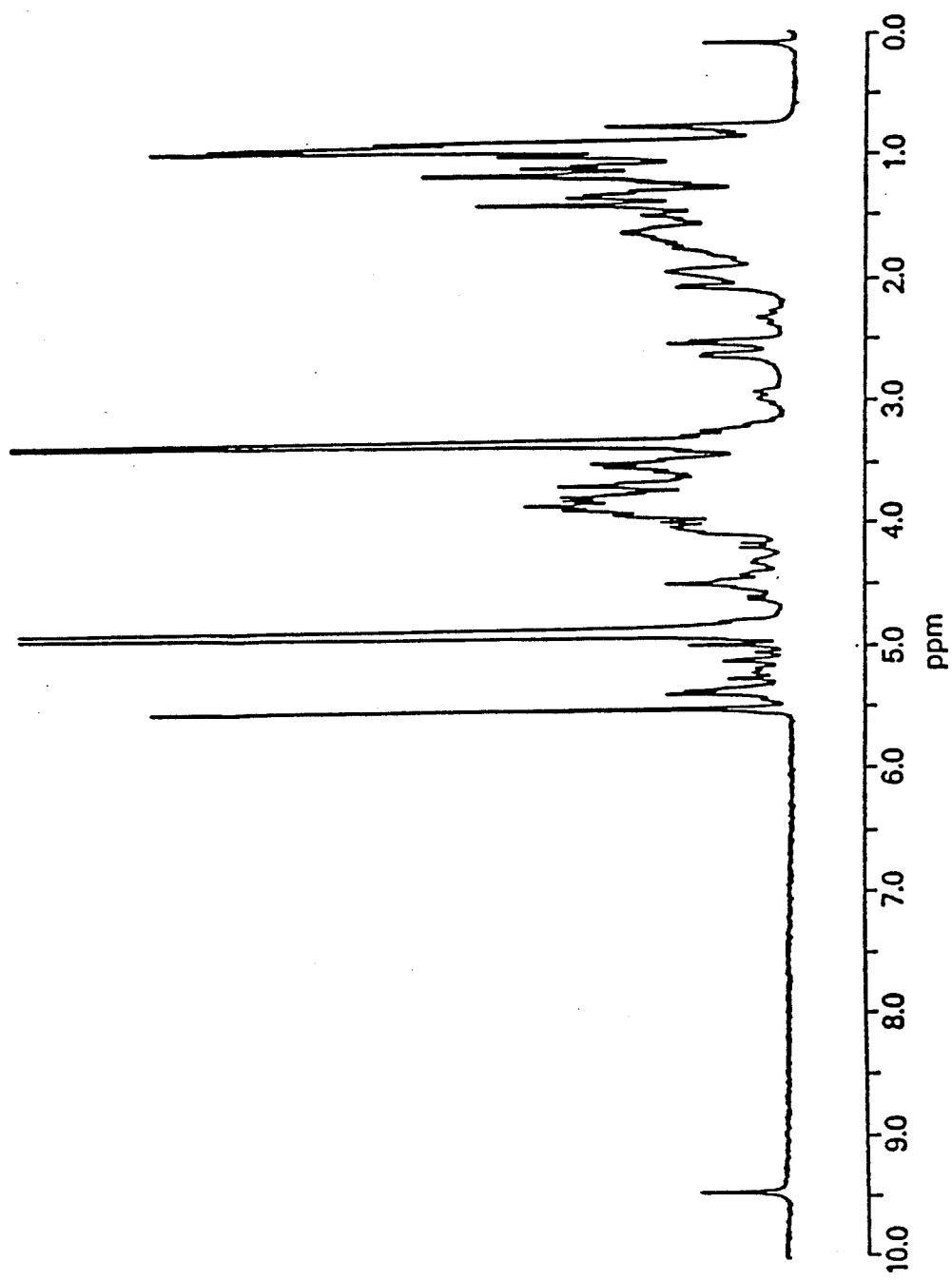
FIG. 7C shows 'H NMR of QA-21.

$^1$H-NMR at 250 MHz of the purified saponins in $CD_3OD$ demonstrates the complex nature of the purified saponins QA-7 (FIG. 7A), QA-18 (FIG. 7B), and QA-21 (FIG. 7C). The signals in the region between 4.1 to 5.4 ppm clearly demonstrate the presence of multiple signals from the anomeric protons of the monosaccharides, indicating a multiplicity of monosaccharide resides. However, the NMR spectra of the saponins are too complex to allow structural determination.

Figure 8A:
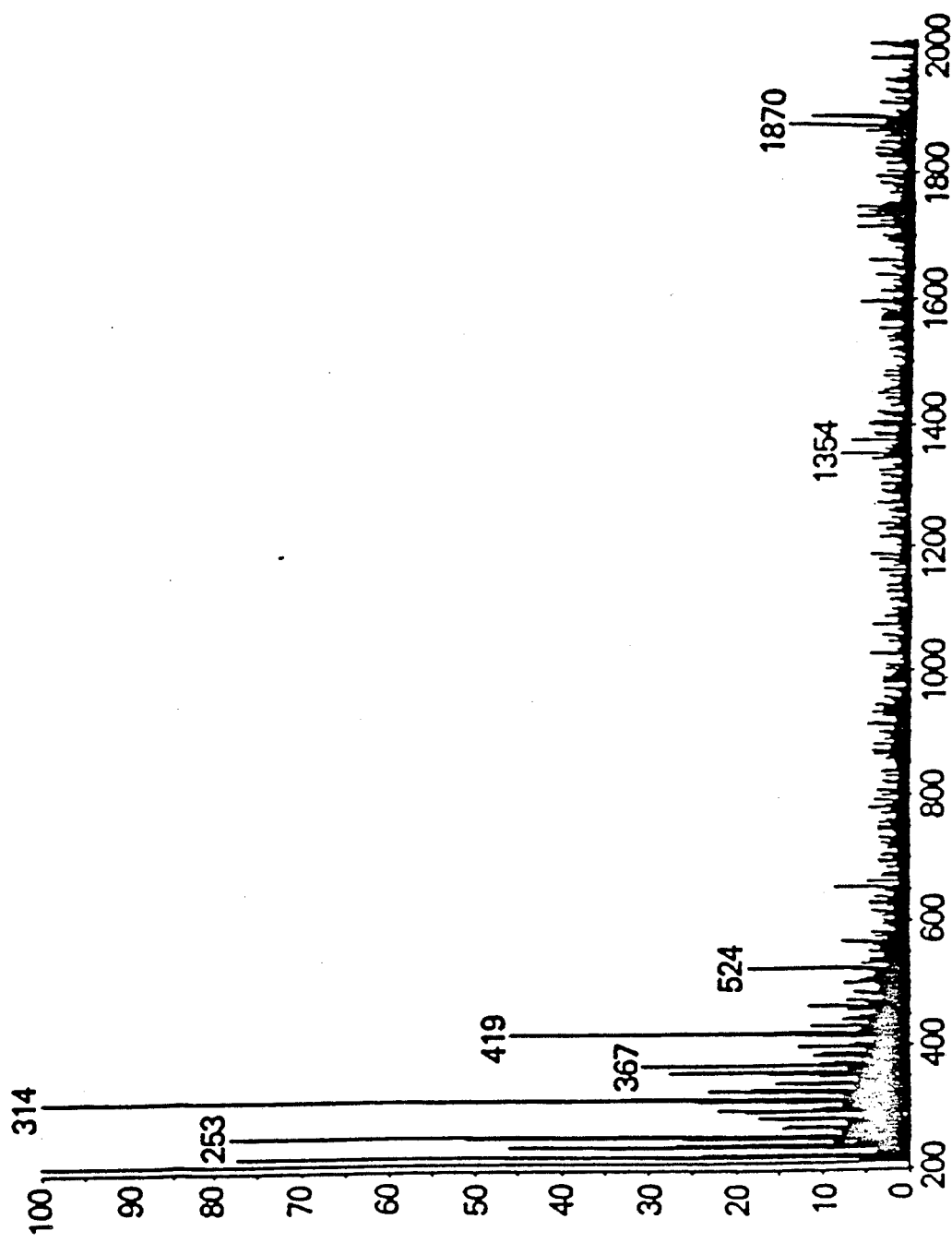
FIG. 8A shows the mass spectroscopy-fast atom bombardment ("MS-FAB") spectrum of QA-7.
Figure 8B:
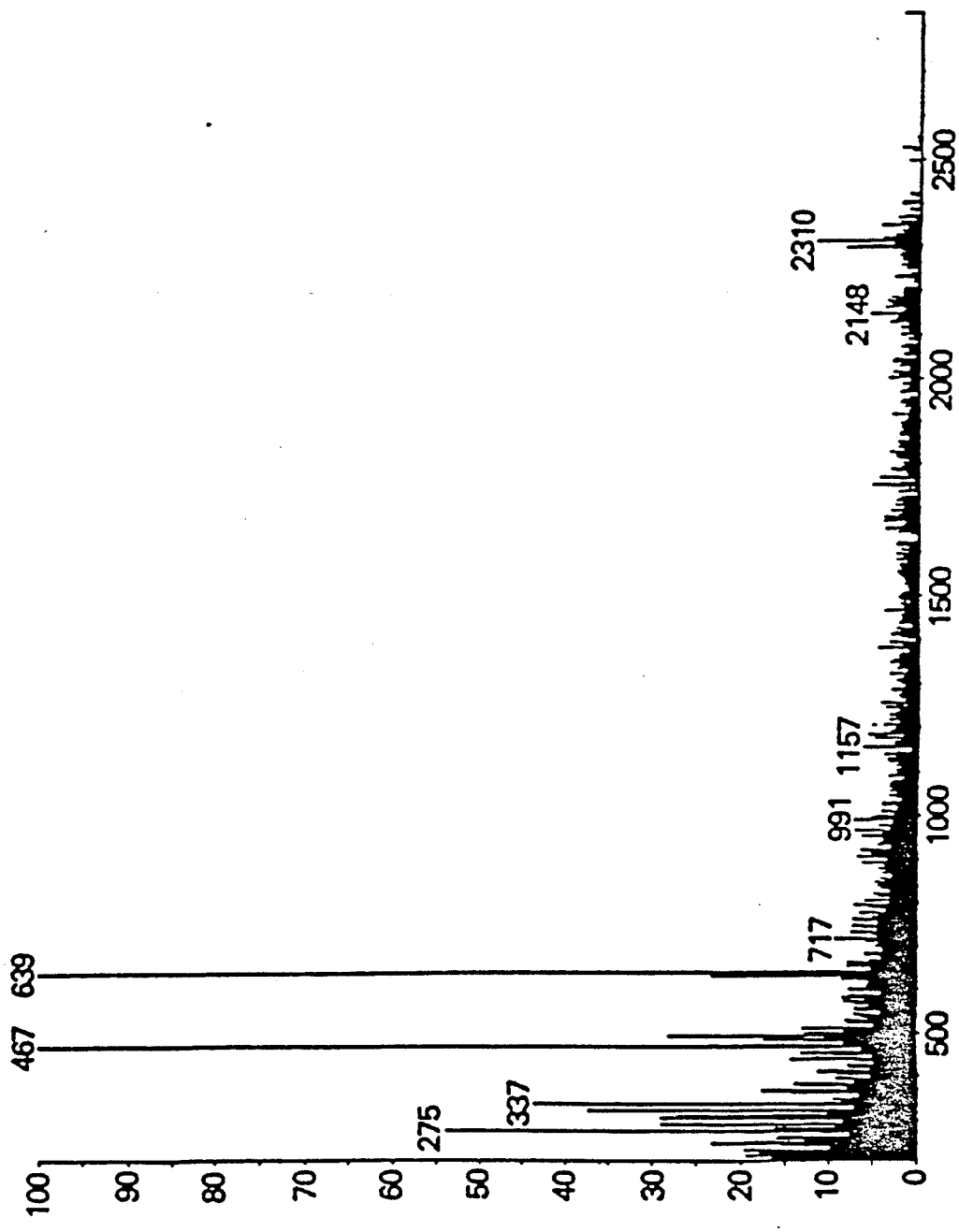
FIG. 8B shows the MS-FAB spectrum of QA-17.
Figure 8C:
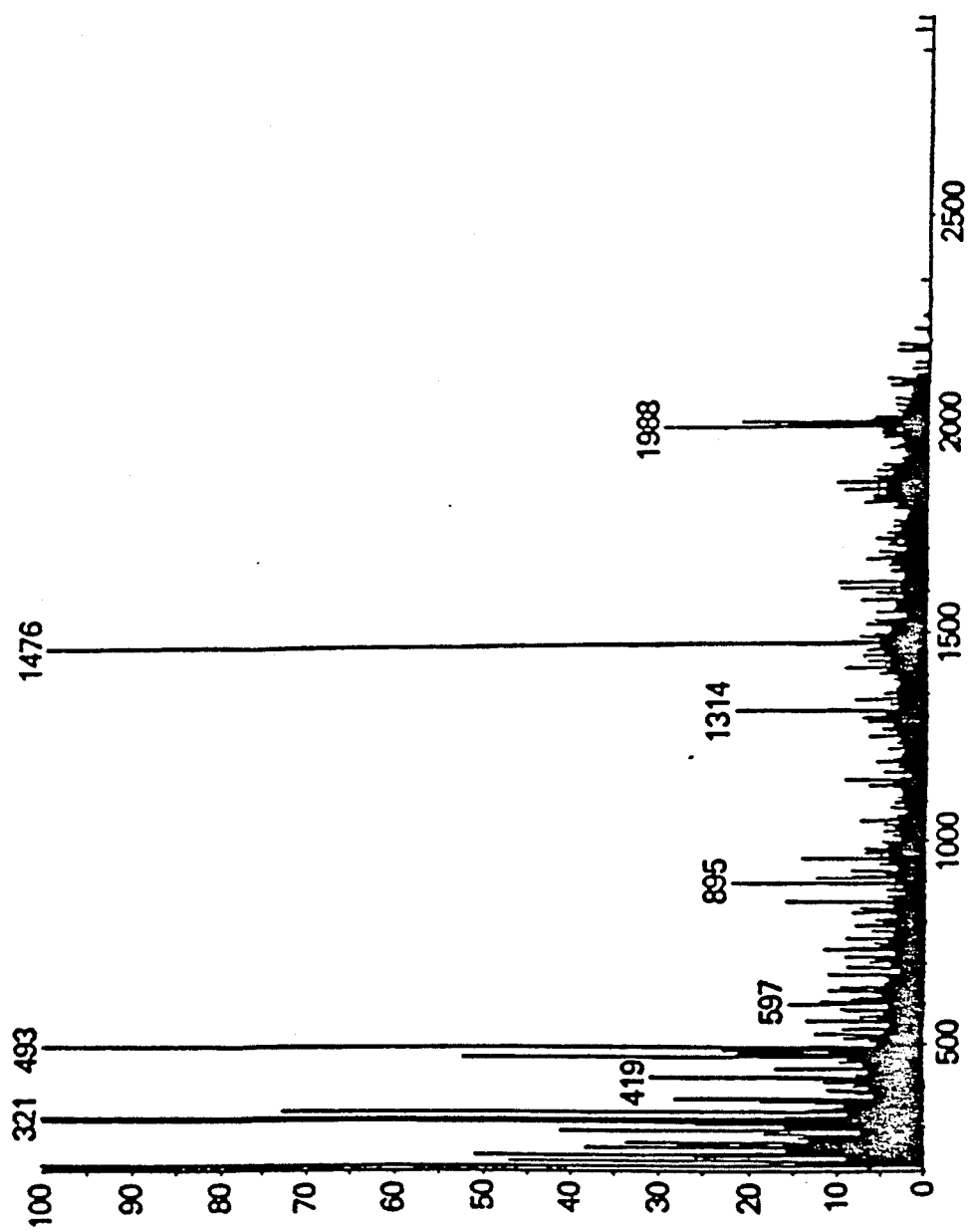
FIG. 8C shows the MS-FAB spectrum of QA-21.

MS-FAB of the purified saponins QA-7, QA-17, and QA-21 (FIGS. 8A, 8B, 8C, respectively) indicated approximate pseudo- molecular ion masses of 1870, 2310, and 1980, respectively. MS-FAB was not determined on QA-18 due to difficulties in solubilizing this component. These molecular weights are consistent with those expected for a triterpene linked to eight to ten monosaccharide residues and were in the same range as monomer molecular weights determined by size exclusion HPLC of purified saponins in methanol (Zorbax PSM 60 Si column, 25 cm×6.2 mm, 1 ml/min flow rate, molecular weight standards=18-β-glycrhetinic acid and ginenoside $Rb_1$) which indicated approximate molecular weights of 2600, 2400, 1800, and 2400 for QA-7, QA-17, QA-18, and QA-21, respectively. The difference between FAB-MS and size exclusion HPLC are most likely due to variation in shape between the saponins and the molecular weight standards.

Carbohydrate Composition

Table 3 below shows the carbohydrate composition and linkage analysis of purified saponins QA-7, QA-17, QA-18, QA-21, and QA-19. The carbohydrate in saponins was converted to alditol acetates by heating 0.2 mg saponin in 0.3 ml 2N trifluoroacetic acid containing 0.1 mg/ml inositol at 120° C. for two hours. The acid was removed under a flow of air, and residual acid removed by the addition of isopropanol (2×0.25 ml), followed by blowing to dryness with air. The dry residue obtained was dissolved in 1M ammonium hydroxide (0.25 ml) containing 10 mg/ml sodium borodeuteride and kept for one hour at room temperature. Glacial acetic acid (0.1 ml) was added, and the solution was blown to dryness. Residual borate was removed by co-distilling with 10% acetic acid in methanol (3×0.25 ml) and finally with methanol (2×0.25 ml). The dry residue in acetic anhydride (0.1 ml) and pyridine (0.1 ml) was heated for 20 minutes at 120° C. Toluene (9.02 ml) was added to the cooled solution, and the solvents removed under a flow of air. This procedure of adding toluene and removing pyridine and acetic anhydride was repeated twice. The residue obtained was taken up in dichloromethane (0.5 ml) and extracted with water (0.5 ml). The organic phase was transferred to a clean tube and dried. Prior to analysis by GLC (gas-liquid chromatography), the residue was dissolved in acetone (0.1 ml). Alditol acetates were analyzed on an SP2330 capillary GLC column (30 m×0.25 mm) at 235° C.) with flame ionization detection. The carbohydrate in saponins was converted to trimethylsilated methylglycosides by heating 0.1 mg of sample in methanolic HCl (0.3 ml) containing 50 ug/ml inositol for 16 hours at 80° C. The sample was blown to dryness, and residual acid removed by the addition of t-butyl alcohol (2×0.25 ml) followed by drying with a flow of air. The dry residue was dissolved in a solution (0.2 ml) containing pyridine, hexamethyldisilazane, and trimethylchlorosilane (5:1:0.5 v/v, "Tri-Sil") and heated for 20 minutes at 80° C. The silylating reagent was evaporated at room temperature, and the residue dissolved in hexane (1 ml). After removal of the insoluble residue by filtration using glass wool plug, the filtrate was transferred to a clean tube and evaporated. The residue was dissolved in hexane (0.2 ml) prior to analysis by GLC. The trimethylsilated methyl glycosides were analyzed on a GLC column of fused silica DB1 (25 m×0.25 mm) for 3 min at 160° C. followed by a 2°/min increase to 200° C. and then a 10°/min increase to 260° C. with flame ionization detection.

Glycoside linkage analysis was carried out by the following method: To the sample ($\approx$1 mg) dissolved in dry dimethylsulfoxide (0.2 ml), 0.2 ml of potassium dimethylsulphinyl anion (2M) was added, and the mixture stirred for 12 hours under argon. The reaction mixture was cooled in ice, and methyl iodide (0.2 ml) was added drop wise. The resulting mixture was sonicated and stirred at room temperature for one hour. The methylated material was isolated using Sep-Pak $C_{18}$ cartridges conditioned with ethanol (20 ml), acetonitrile (8 ml), and water (10 ml). Water (1 ml) was added to the methylation reaction mixture, and the excess methyl iodide removed by passing nitrogen through the solution. The clear solution was applied to the cartridge which was washed with water (8 ml) and 20% acetonitrile (5 ml). The methylated material was eluted from the cartridge with 100% acetonitrile (4 ml) and ethanol (4 ml). The solvents were removed with a flow of air. The dried methylated material was treated with 0.3 ml of "super deuteride" solution at room temperature for one hour in order to reduce the uronic acid residues to the corresponding hexoses. After destroying the excess reagent with glacial acetic acid (0.1 ml), the reaction mixture was blown to dryness with 10% acetic acid/methanol and blown to dryness two more times. The resulting reduced methylated material in methanol was passed through a column of Dowex—50 W(H+) and the effluent obtained was dried. The reduced methylated material was converted to methylated alditols as described in section 1 above and analyzed by GLC (SP2330 fused silica column (30 m×0.25 mm), 3 min at 170° C. followed by 4°/min to 240° C.) and GLC-MS (SP2330 fused silica column (30 m×0.25 mm), 2 min at 80° C. followed by 30°/min to 170° C. followed by 4°/min to 240° C. followed by holding at 240° C. for 10 min, mass spectral analysis on Hewlett-Packard MSD).

Despite the similarity in the carbohydrate composition, subtle differences distinguish the individual saponins, in particular, the absence of arabinose in QA-7 and decreased glucose in QA-21 compared to the other saponins.

TABLE 3

Carbohydrate Composition and Linkage Analysis of Purified Saponins

| | QA-7 | | | QA-17 | | | QA-18 | | | QA-19A | | | QA-21 | | |
|---|---|---|---|---|---|---|---|---|---|---|---|---|---|---|---|
| | AA[a] | TMS[b] | Linkage | AA | TMS | Linkage | AA | TMS | Linkage | AA | TMS | Linkage | AA | TMS | Linkage |
| rhamnose | 191.4 | 1.57 | T[c] 3,4 | 184.8 | 1.9 | T 3,4 | 132.0 | 0.99 | T 3,4 | 32.7 | 1.69 | T 3,4 | 131.9 | 1.07 | T 4 |
| fucose | 86.7 | 0.67 | 2,3 | 77.9 | 0.78 | 2 | 95.6 | 0.76 | 2 | 26.6 | 0.88 | 2 | 99.8 | 0.76 | 2 |
| arabinose | trace | trace | | 65.4 | 0.80 | 2 | 80.1 | 0.64 | T | 31.1 | 0.94 | T | 71.0 | 0.65 | T |
| xylose | 98.1 | 0.95 | T 3 | 81.8 | 1.08 | T 3 | 117.8 | 1.16 | T 3 | 49.9 | 2.07 | T 3 | 114.3 | 1.21 | T 3 |
| galactose | 81.2 | 0.74 | T | 69.4 | 0.81 | T | 88.1 | 0.86 | T | trace | 1.11 | T | 88.1 | 0.84 | T |
| glucose | 81.2 | 1.0 | T | 85.7 | 1.0 | T | 89.2 | 1.00 | T | trace | 1.0 | T | 19.6 | 0.30 | T |
| glucuronic acid | N.T.[d] | 0.48 | 2,3 | N.T. | 0.52 | 2,3 | N.T. | 0.62 | 2,3 | 29.2 | 0.62 | 2,3 | N.T. | 0.62 | 2,3 |
| apiose[e] | 22.5 | N.T. | | 24.5 | N.T. | | 25.7 | N.T. | T | 27.7 | | T | 20.0 | N.T. | T |

[a]Alditol acetate (μg/mg saponin)
[b]Trimethylsilated methyl glycosides (relative proportions)
[c]T-terminal glycosyl residue, that is, attached through C-1 but with no other residues attached to it. 3,4 = a glycosyl residue attached through C-1 with other glycosyl residues glycosidically attached to it through C-3 and C-4.
[d]Not tested
[e]Poor recovery as alditol acetates Characterization of Saponins as Detergents The critical micellar concentration of adjuvants QA-7, QA-17, QA-18, and QA-21 was determined by the method of DeVendittis et al. (DeVendittis, E., Palumbo, G., Parlato, G., and Bocchini, V. (1981) *Anal.*

Biochem. 115, 278-286) as follows: The emission spectrum of 1-anilinonapthalene-8-sulfonic acid (ANS) in water was determined at dry weight concentrations of adjuvant ranging from 0.01 to 0.10% (W/v) to cover the range below and above the critical micellar concentration. Above the critical micellar concentration, the fluorescence yield of ANS increases and the wavelength of maximum emission decreases due to partitioning of the fluorescent dye into the micelles. Similar critical micellar concentrations were found for QA-7, QA-17, QA-18, and QA-21 in water (0.06%, 0.06%, 0.04%, and 0.03%, respectively) with slightly lower concentrations determined in phosphate buffered saline (0.07% 0.03%, 0.02%, and 0.02%, respectively).

Figure 9:
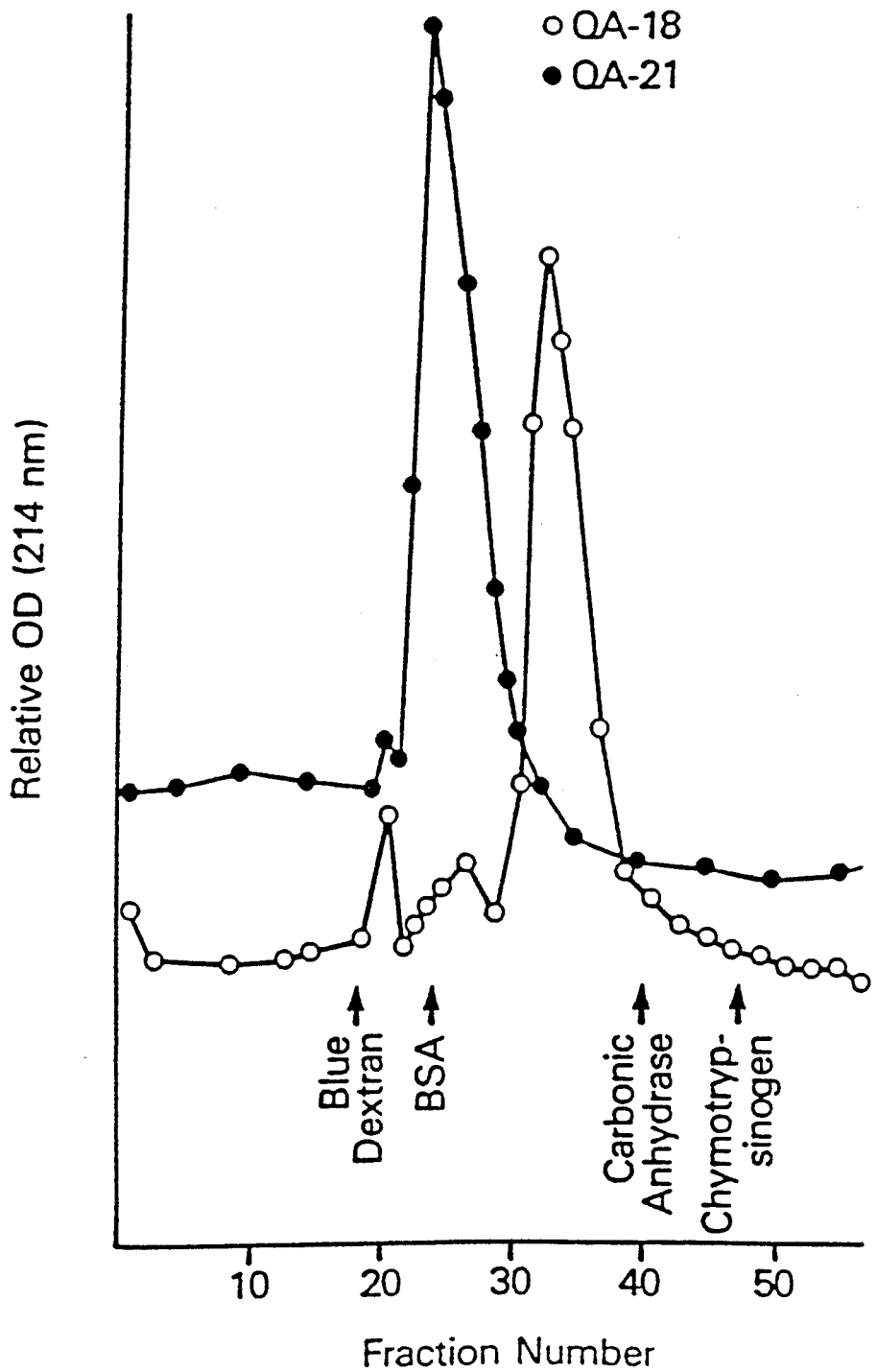
FIG. 9 shows the elution profile of pure QA-18 micelles and pure QA-21 micelles by gel filtration on Bio-Gel P-200 in PBS equilibrated with the critical micellar concentration of the same saponin and a comparison with the elution position of standard proteins.
Figure 10:
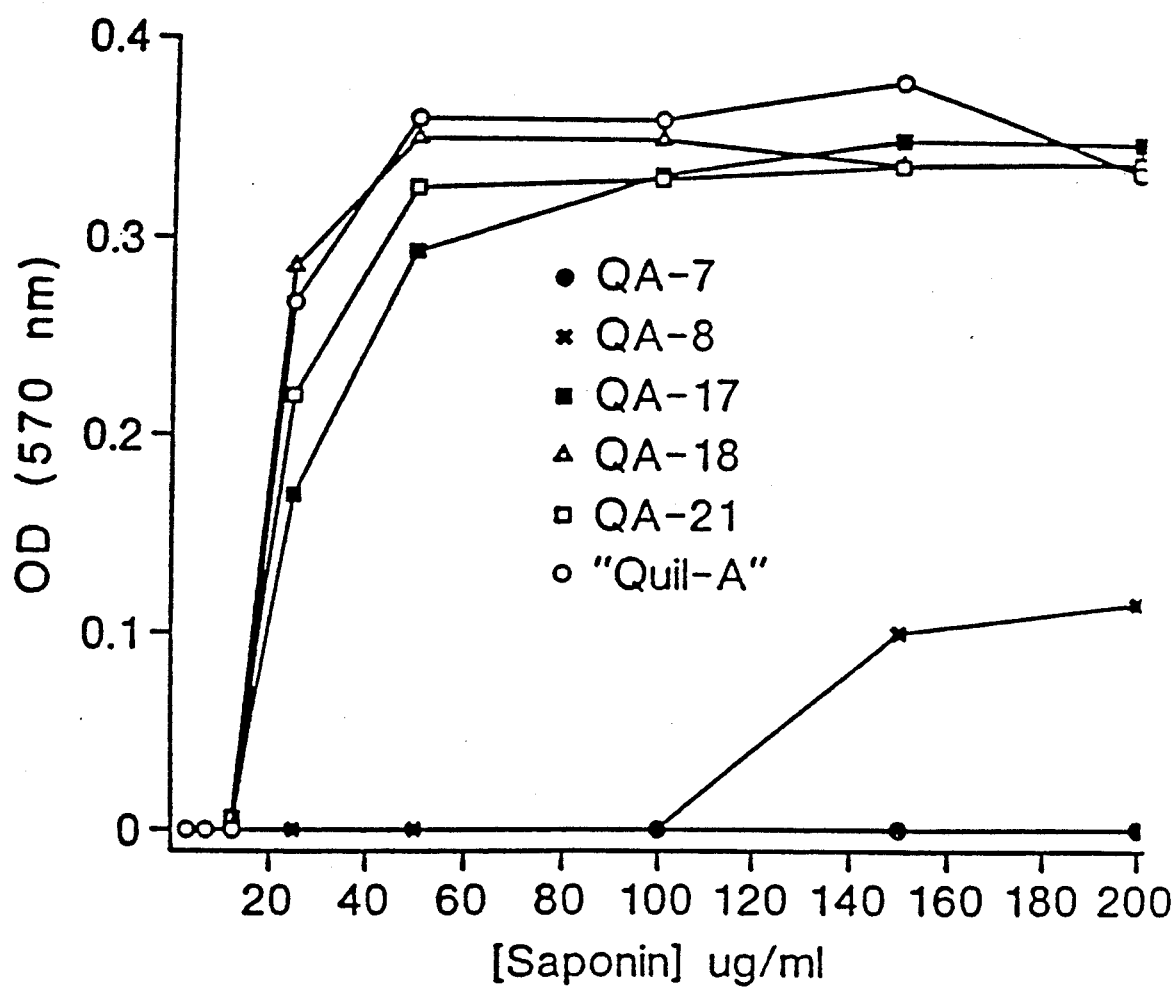
FIG. 10 shows the hemolysis of sheep red blood cells by QA-7, QA-8, QA-17, QA-18, QA-21, and Superfos "Quil-A."

FIG. 9 shows the gel filtration chromatograph for micelles formed by purified QA-18 and QA-21 (on Bio-Gel P-200 (6.6 mm ID×90 cm ht)), pre-equilibrated in a concentration of purified saponin equivalent to the critical micellar concentration of that saponin in phosphate buffer saline to prevent the monomer-micelle equilibrium from reducing the apparent radius of the micelles). QA-18 and QA-21 micelles elute with a size that is similar to that of the protein bovine serum albumin.

The hemolytic activity of the adjuvants was determined by the following method: Dilutions of adjuvants QA-7, QA-8, QA-17, QA-18, QA-21, and Superfos "Quil-A" were made on a round bottom , microtiter plate (75 μl per well). Sheep red blood cells (SRBC), washed three times with PBS, were diluted to 4% with PBS. SRBC (25 μl) were added to each well and mixed with adjuvant. After incubation at room temperature 30 min, the plates were spun at 1000 rpm 5 min in a Sorvall RT6000, H-1000 rotor, to sediment unhemolyzed cells. 50 μl of the supernatant from each well was transferred to the same well of a flat bottom microtiter plate and diluted to 200 μl with H$_2$O. Absorbance was determined at 570 nm with a Dynatech microtiter plate reader. (FIG. 9) Hemolysis increased the absorbance at 570 nm due to release of hemoglobin from the lysed cells. Significant differences in hemolysis were observed between adjuvants. QA-17, QA-18, QA-21, and Superfos "Quil-A" caused partial hemolysis at concentrations as low as 25 μg/ml whereas partial hemolysis was observed with QA-8 at 150 μg/ml. No hemolysis was observed with QA-7 at the concentrations tested (200 μg/ml and less).

EXAMPLE 6

Isolation of Toxic Component QA-19

Figure 4A:
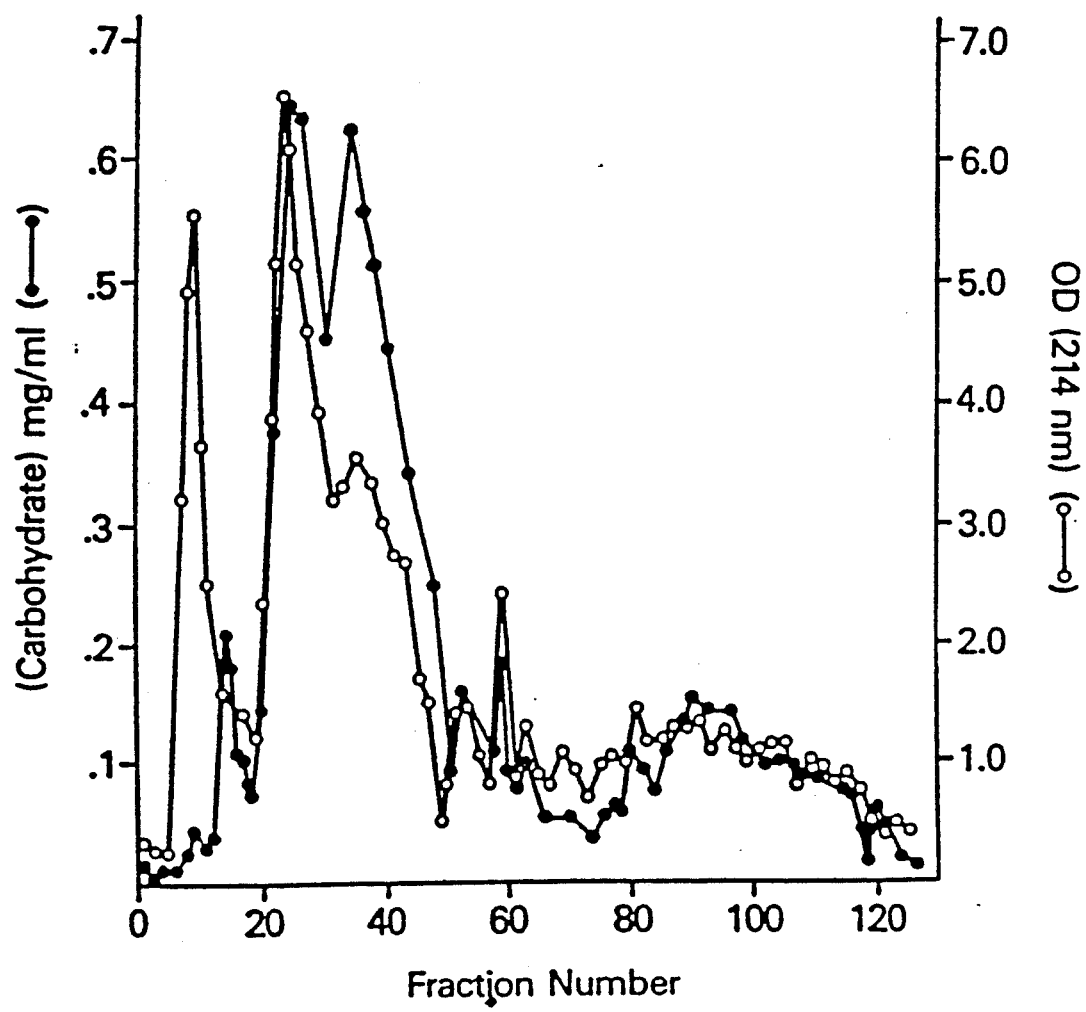
FIG. 4 shows the purification of QA-7, QA-17, QA-18, QA-19, and QA-21 from "Quil-A," a crude saponin mixture, by silica chromatography (4A) and subsequent reverse phase chromatography (4B, 4C, 4D).
Figure 4B:
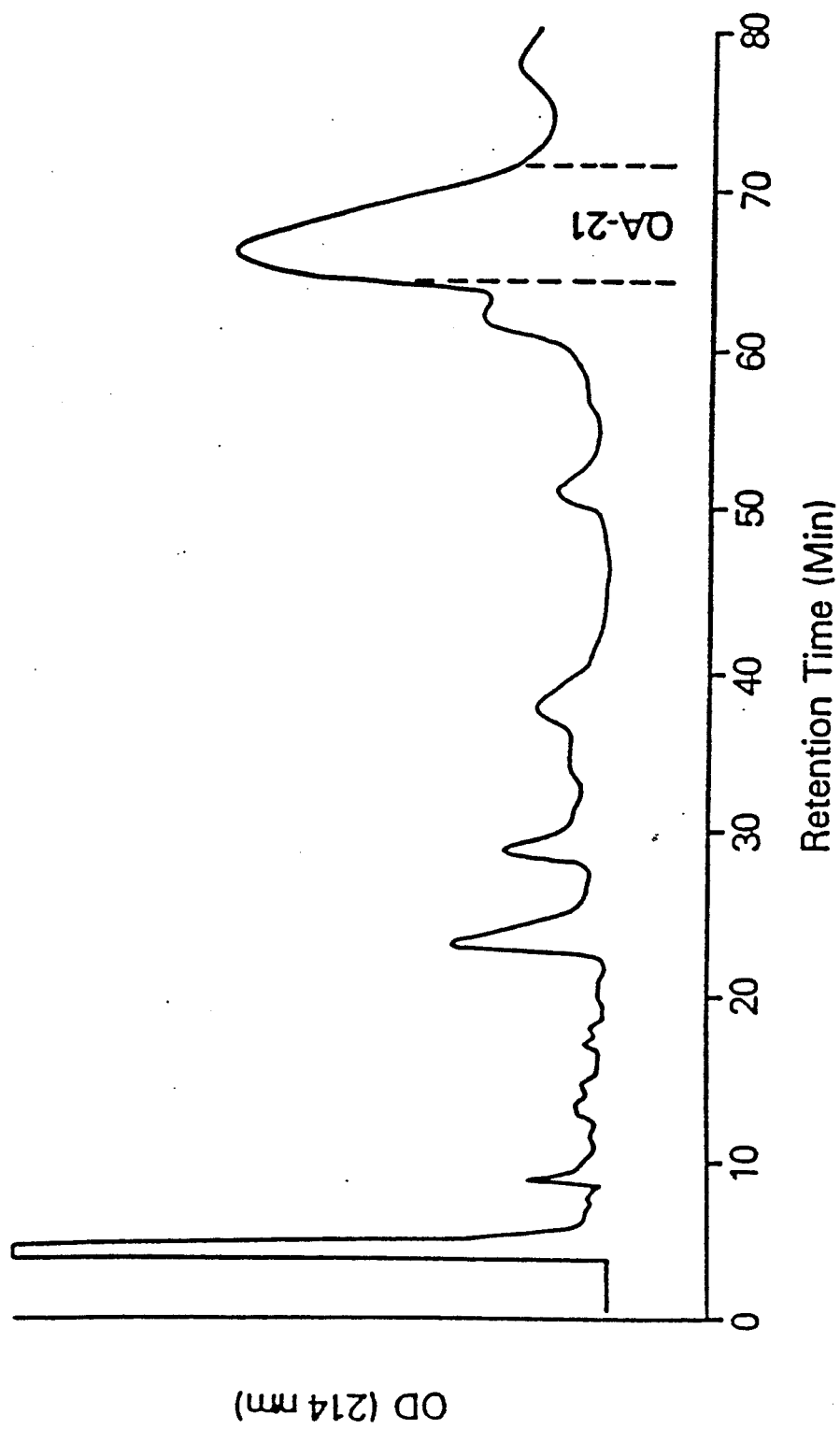
Figure 4C:
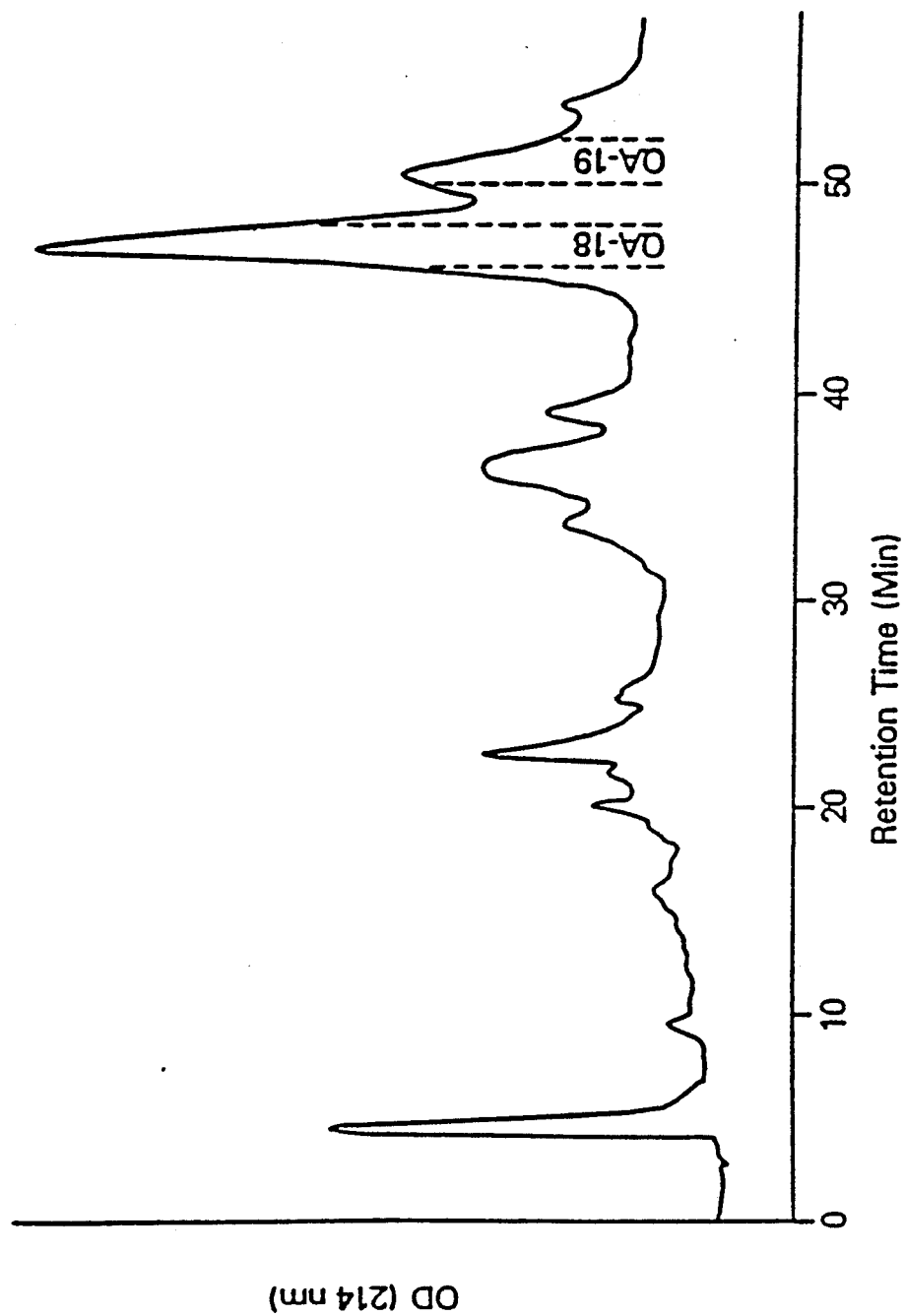
Figure 4D:
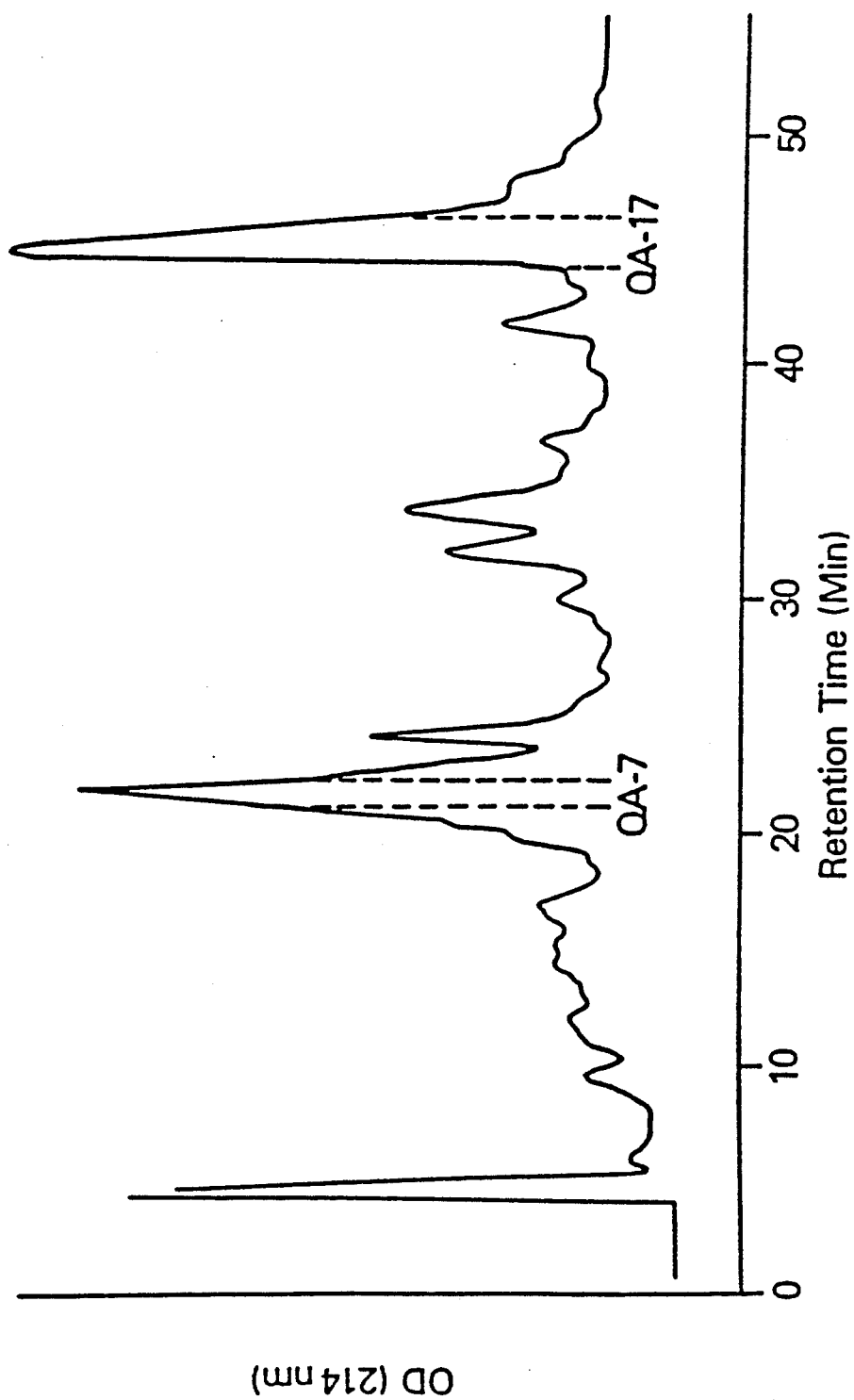

The toxic component QA-19 cochromatographs with QA-18 on silica and is enriched in silica fractions 31-60. These fractions were pooled and flash evaporated prior to further purification. FIG. 4C shows the separation of QA-19 from QA-18 by reverse phase HPLC on Vydac C$_4$ (10 mm ID×25 cm L) using a methanol gradient. Fractions eluting with a retention time between 50-52 minutes were identified as QA-19 by reverse phase TLC and analytical HPLC and pooled for further characterization. QA-19 could be further separated into two peaks by repurification in a shallower methanol gradient, with the peak with shorter retention time designated QA-19a and the peak with longer retention time designated QA-19b. Carbohydrate analysis of peak QA-19a which is more toxic in mice than QA-19b, shows a carbohydrate composition which is similar to that of the other saponins (Table 3).

EXAMPLE 7

Isolation of Alkaline Hydrolysis Product

Treatment of QA-18 by brief alkaline hydrolysis yielded one major carbohydrate-containing alkaline hydrolysis product (designated QA-18 H). Purified QA-18 H was prepared from QA-18 and isolated in the following manner:

One ml QA-18 (5 mg/ml) was incubated with 25 μl 1N NaOH for 15 minutes at room temperature. The reaction was stopped with the addition of 100 μl 1N acetic acid. Using these hydrolysis conditions, QA-18 was completely converted to a major hydrolysis product (QA-18 H) eluting in a peak with retention time of 8.0 min compared to 66.8 min for unhydrolyzed QA-18, indicating the increased hydrophilicity of QA-18 H. (Chromatography on Vydac C$_4$ (4.6 mm ID×25 cm L) in 0.1% trifluoroacetic acid in 55/45 methanol/water v/v) and eluted in a gradient to 64/36 methanol/water (v/v) over 180 minutes, flow rate of 1 ml/minute). The peak containing pure QA-18 H (retention time 8.0 min) was pooled for further characterization. The hydrolysis product of QA-21, designated QA-21 H, was prepared and purified in the same manner. QA-21 H had a retention time of 9.3 minutes compared to 80.4 minutes for unhydrolyzed QA-21. These hydrolysis products were shown by retention time on HPLC and by reverse phase thin layer chromatography to be identical to the major hydrolysis products generated using the method of Higuchi et al., *Phytochemistry* 26: 229 (1987) using mild alkaline hydrolysis in NH$_4$HCO$_3$ (Table 4). In addition, these products, QA-18 H and QA-21 H, were shown to be the major breakdown products from hydrolysis of "Quil-A", a crude saponin mixture containing QA-7, QA-17, QA-18, and QA-21 as well as other saponins, indicating that the hydrolysis products QA-21 H and QA-18 H are the same hydrolysis products isolated by Higuchi et al., supra, for structural characterization. QA-18, H and QA-21 H were saved for further characterization of adjuvant activity.

TABLE 4

| Retention Time of Major Alkaline Hydrolysis Products | |
|---|---|
| QA-17 H | 8.0$^a$ |
| QA-18 H | 8.0$^a$ |
|  | 8.2$^b$ |
| QA-21 H | 9.3$^a$ |
|  | 9.5$^b$ |
| Hydrolyzed - "Quil-A" | 8.2$^a$, 9.3$^a$ |

$^a$Cambridge BioScience hydrolysis conditions: 5 mg/ml saponin, pH 13, reaction time = 15 minutes at room temperature
$^b$Higuchi et al. hydrolysis conditions: 5 mg/ml saponin, 6% NH$_4$HCO$_3$, methanol/-H$_2$O (1/1, v/v), reaction time = 60 minutes at 100° C.
HPLC Conditions:
Vydac C$^4$, 5 μm particle size, 300 Å pore size, .46 × 25 cm
Solvent A = 0.1% trifluoroacetic acid in water
Solvent B = 0.1% trifluoroacetic acid in methanol
Gradient = 55–64% B/180 minutes
Flow rate — 1 ml/min

EXAMPLE 8

Testing for Adjuvant Effect Using BSA as Antigen

Briefly, adjuvant effect is assessed by increase in antigen-specific antibody titers due to addition of potential adjuvant in the immunization formulation. Increased titers result from increased antibody concentrations and/or increased antigen/antibody affinity. Adjuvant effects of saponins have previously been measured by increase in titer of neutralizing antibodies to foot-andmouth disease vaccines in guinea pigs (Dalsgaard, K., *Archiv. fur die gesamte Virusforschung* 44, 243–254 (1974)), increase in titer of precipitating antibodies to BSA (as measured by radial immunodiffusion) in guinea pigs vaccinated with BSA/saponin mixtures (Dalsgaard, K. *Acta Veterinaria Scandinavica* 69, 1–40 (1978)), as well as by the increase in titer of anti-keyhole limpet hemocyanin (KLH) antibody (measured by ELISA) in mice immunized with KLH/saponin (Scott, M. T., Gross-Samson, and Bomford, R., *Int. Archs. Allergy Appl. Immun.* 77:409–412 (1985)).

Figure 11:
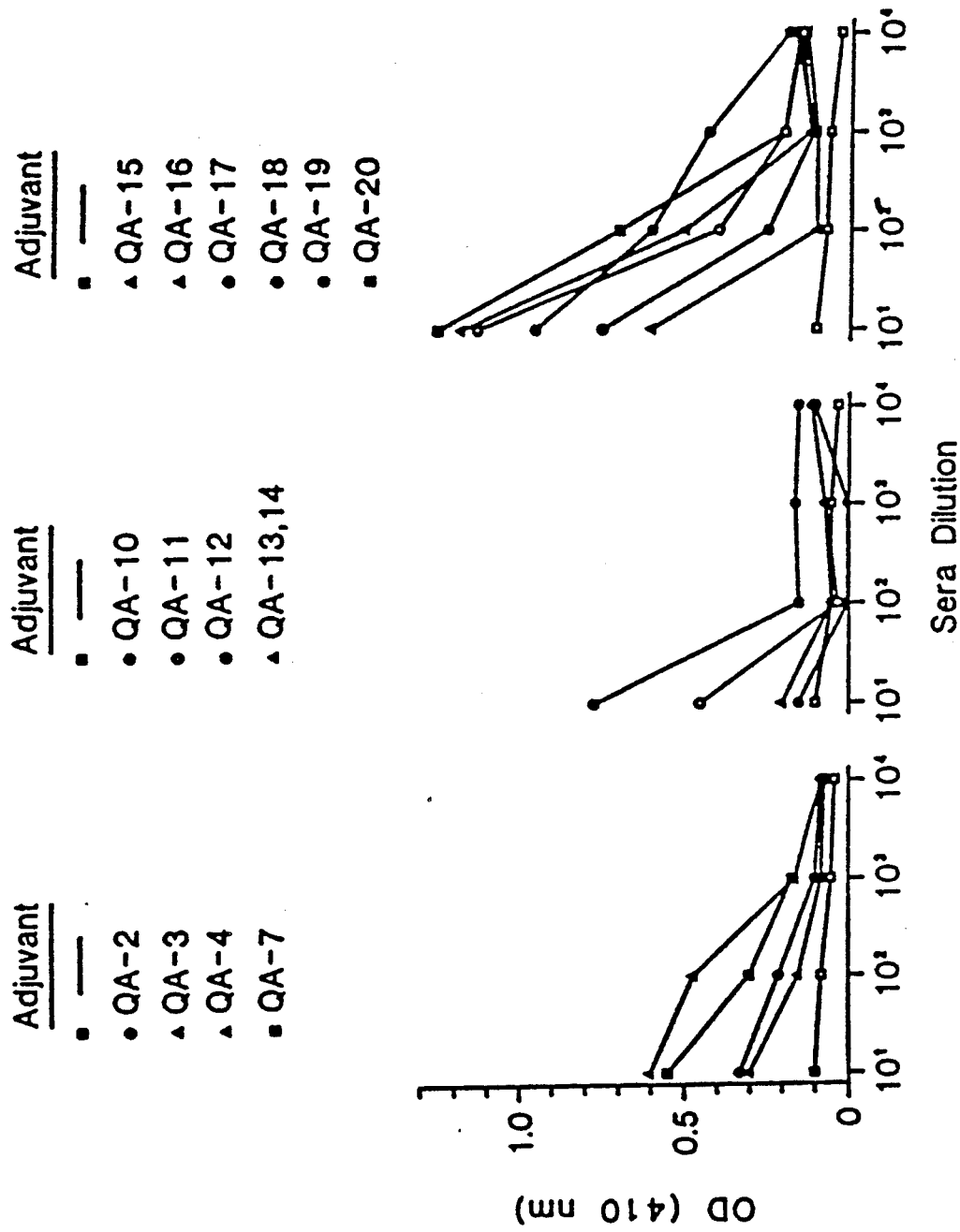
FIG. 11 shows the typical endpoint titers for immunization with BSA antigen in the presence of HPLC-purified fractions of bark extract. Absorbance due to antigen-specific antibody binding was plotted as a function of the logarithm of the sera dilution.

Assessment of adjuvant effect in this study was determined by increase in anti-BSA antibody following immunization with BSA/saponin compared with immunization with BSA in the absence of saponin. The adjuvant activity in the purified fraction was measured as follows: CD-1 mice (8–10 weeks old) were immunized intradermally with the following formulation: 10 μg BSA (Sigma 7030, fatty acid free) and Quillaja adjuvant (at doses ranging from 1.5–45 μg carbohydrate as measured by anthrone) in 200 μl PBS. Sera was harvested two weeks post-immunization. Anti-BSA antibody was determined by ELISA: Immulon II plates were coated overnight at 4° C. with 100 μl fatty acid free BSA (10 μg/ml in PBS) in rows, A, C, E, and G. Plates were washed twice with PBS. Nonspecific binding was prevented by incubating for 1.5 h at 37° C. with 100 μl diluent (2% Casein acid hydrolysate (Oxoid, w/v) in PBS) per well in all wells. Plates were washed four times with 0.05% Tween 20 in distilled water. Sera at dilutions of 10, $10^2$, $10^3$, and $10^4$ were incubated in rows A+B, C+D, E+F, and G+H, respectively (100 μl/well) for 1 h at room temperature. Plates were washed as described above. Boehringer-Mannheim horse radish peroxidase conjugate goat anti-mouse antibody (1/5000 in 5% BSA in diluent) was incubated for 30 min at room temperature (100 μl per well, all wells). Plates were washed as described above. The extent of peroxidase reaction was determined by reaction with 2,2'-azino-bis(3-ethylbenzthiazoline)-6-sulfonate (30 minute reaction at room temperature, absorbance measured at 410 nm) or with 3,3',5,5'-tetramethylbenzidine (10 min reaction at room temperature, absorbance measured at 450 nm). The contribution of nonspecific antibody binding to the total antibody binding was removed by subtraction of the absorbance of the antigen-negative well from the absorbance of the antigen-positive well for each sera dilution. The absorbance due to antigen-specific binding was plotted as a function of the logarithm of the sera dilution. (FIG. 11) Typical endpoint titers were typically at a sera dilution of 10 or less for immunization in the absence of adjuvant and were as high as $10^3$ in the presence of saponin adjuvant. Dialyzed, methanol-soluble bark extract at an adjuvant dose of 12 μg carbohydrate or greater (carbohydrate assayed by anthrone) increased titers by 2 orders of magnitude compared to BSA in PBS. A good adjuvant effect was observed at doses of "Quil-A" between 9–23 μg carbohydrate.

EXAMPLE 9

Adjuvant Testing of HPLC-Purified Extract Components

By the criteria described in Example 8, peaks QA-7, QA-11, QA-12, QA-15, QA-16, QA-17, QA-18, QA-19, and QA-20 have varying degrees of adjuvant effect with QA-15, QA-17, QA-18, QA-19, and QA-20 being particularly effective at a dose of 3.0 μg carbohydrate in this particular experiment. Due to the small number of mice used per immunization (2) and the natural variation in immune response between individual mice, this experiment cannot be used to quantitatively assess the relative adjuvant effect of these peaks. However, it provides a qualitative assessment of the presence of adjuvant activity. It must also be noted that the absence of apparent effect with QA-2, QA-3, QA-10, QA-13, and QA-14 does not rule out an adjuvant effect at different adjuvant doses or adjuvant/protein ratio.

Figure 12:
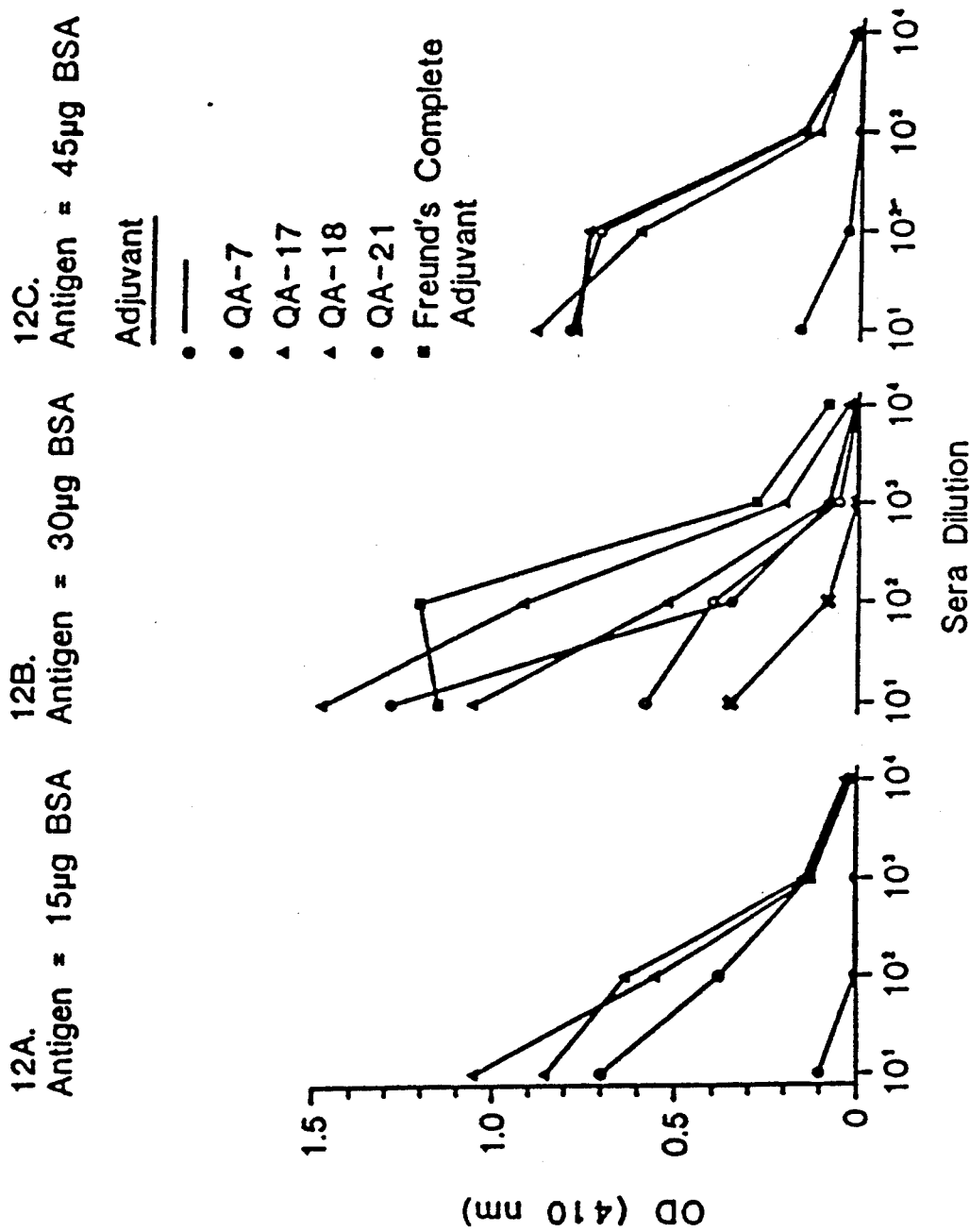
FIG. 12 demonstrates the comparison of the adjuvant effects of QA-7, QA-17, QA-18 and QA-21 at various antigen concentrations and with Freund's complete adjuvant on immunization with the antigen BSA.

Further adjuvant studies were carried out with QA-7, QA-17, and QA-18 at different protein/adjuvant ratios. In general, a good adjuvant effect was observed for QA-7, QA-17, and QA-18 when used at protein/adjuvant ratios (protein weight/carbohydrate weight) of approximately 3:1 to 9:1 (FIG. 12). QA-21 (tested in this study only at protein/carbohydrate weight of 6:1) also showed an adjuvant effect. However, it should be noted that the proper adjuvant to protein ratio for optimum immune response is a function of both the particular saponin adjuvant and the particular antigen used. Adjuvant association with antigen plays an important role in the mechanism of action of the saponin adjuvant effect. In the case of saponin binding to protein, hydrophobic interactions are the predominant factor. Hence, differences in hydrophobicity of the HPLC-purified adjuvants will affect the binding constant to hydrophobic proteins. In addition, the number of hydrophobic binding sites on the protein will also affect the ability to associate with saponin adjuvants. Hence, it is necessary to determine the optimum adjuvant dose for each individual adjuvant and antigen. Such optimization is within the skill of the art.

HPLC-purified adjuvants were also compared with Freund's complete adjuvant and were found to result in a similar level of immune response (FIG. 12, panel b).

EXAMPLE 10

Preparation of FELV Recombinant gp70R-delta

Inclusion Body Preparation

Recombinant *E. coli* clone R16-38 was grown in LB medium supplemented with 1% glucose and 0.1% casamino acids at 32° C. to an optical density (560 nm) of 0.4–0.6. The culture was then shifted to 42° C. and incubated for an additional 2 hours. At the end of this time the cells were collected by centrifugation at 4,000 g for 30 minutes, washed with 50 Tris HCl, pH 7.5, and finally resuspended in 200 ml 50 Tris HCl to which is added 1 ml 0.1M phenylmethylsulfonylfluoride in isopropanol (final concentration 0.5 and 0.4 ml of 5 mg/ml aprotinin (final concentration=10.0 ug/ml). The cells were lysed by enzymatic digestion with lysozyme (final concentration=0.5 mg/ml) in the presence of 0.2% Triton X-100. After stirring for 30 minutes, 2 ml MgCl$_2$ (0.5M), 5 ml DNaseI (1 mg/ml) and 1 ml 0.1M phenylmethylsulfonylfluoride were added. After stirring for 30 additional minutes, 40 ml EDTA (0.25M, pH 7.5) and 4 ml Triton X-100 (10% w/v) were added. The preparation was centrifuged at 10,000×g for 30 minutes at 4° C., and the pellet was resuspended in 50 ml 50 Tris HCl, pH 7.5. The pellet was homogenized at low speed for 15 seconds. Lysozyme was added to a concentration of 0.5 mg/ml and 0.6 ml of 10% Triton X-100 were added. After stirring for 15 minutes, 10 ml of MgCl$_2$ (0.5M) and 1 ml DNase I (1 mg/ml) were added and stirring was continued for an additional 15 minutes. After adjusting the volume to 300 ml with 50 Tris, pH 9.0, 40 ml of 10%

Triton X-100 and 51.2 ml of EDTA (0.25M, pH 7.5) were added and the final volume adjusted to 400 ml with 50 Tris, pH 9.0. After stirring for 30 minutes, the suspension was centrifuged at 10,000×g for 30 minutes at 4° C., and the pellet was resuspended in 400 ml 50 Tris HCl, pH 7.5, containing 4M urea, 50 EDTA, and 1% Triton X-100. After stirring for 15 minutes, the suspension was centrifuged at 10,000×g for 30 minutes at 4° C., and the pellet was resuspended in 400 ml 50 Tris HCl, pH 7.5, containing 1.0M NaCl. After stirring for 15 minutes, the suspension was centrifuged at 10,000×g for 30 minutes at 4° C., and the pellet was resuspended in 400 ml 50 Tris HCl, pH 7.5, containing 6M urea, and 5 EDTA. After stirring for 15 minutes, the suspension was centrifuged at 10,000×g for 30 minutes at 4° C. At this point the pellet of inclusion bodies was either frozen for future use or solubilized in 50 Tris HCl, pH 9.5, containing 6M guanidine HCl, 50 EDTA, and 0.5% beta-mercaptoethanol. The gp70R-delta polypeptide was then purified by either of the methods of Example 11, below.

EXAMPLE 11

Purification of FeLV Recombinant gp70R-delta

Procedure I

The solubilized protein of Example 8 was dialyzed against 6M urea, 50 Tris-Cl, pH 8.0, 5 EDTA, and 1 dithiothreitol (DTT). Approximately 120 mg of the protein was applied to a CM-TSK column (EM Science, 1.5 cm ID×4 cm) equilibrated with the same buffer. The protein was eluted with a linear gradient of NaCl (0–1.0M in 150 ml) in the same buffer. The fractions were collected and analyzed by electrophoresis on 10% SDS-polyacrylamide gels. Coomassie-staining was used to identify the gp70R-delta protein. Fractions 25–31, eluting at approximately 0.1M NaCl, were pooled and used for immunization.

Procedure II

In order to decrease the hydrophobicity of gp70R-delta, the sulfhydryl groups were alkylated with iodoacetamide and the lysine residues were N-acylated with citraconic anhydride. The protein prepared as in Example 8 was solubilized in 6M guanidine-HCl in 50 mM borate, pH 9.0, 0.5% beta-mercaptoethanol (v/v). Iodoacetamide is added at a molar ratio of 1:1 (iodoacetamide:total sulfhydryl groups). The alkylation was carried out in the dark for 1 hour at room temperature. The alkylation of all sulfhydryl groups (in the protein and beta-mercaptoethanol) was monitored with DTNB (Ellman's reagent) to ensure complete alkylation. The protein concentration was adjusted to 2 mg/ml.

The protein was citraconylated in the dark by the addition of citraconic anhydride (0.0022 ml per mg protein; approximately 50 molar excess over free lysines). The preparation was dialyzed several times in the dark against 50 mM borate, pH 9.0. The completion of the acylation of the protein lysine groups was determined by reaction with trinitrobenzene sulfonic acid (TNBS) which measures residual free lysine groups. TNBS (200 μl of 10 mM) was added to 200 μg alkylated, citraconylated, dialyzed gp70R-delta in 1 ml 50 mM sodium borate, pH 9.0. The mixture was incubated for 2 hours in the dark at 40° C., the reaction quenched with 0.5 ml of 1N HCl and 0.5 ml 1% SDS, and the absorbance was read at 340 nm. The concentration of TNP-lysine was determined using a molar extinction coefficient of 10,400.

The purification of the alkylated, citraconylated gp70R-delta was performed at pH 9.0 to prevent deblocking of lysine groups. Urea at a final concentration of 4M was added to the modified protein. The protein was concentrated to 3 mg/ml by ultrafiltration and applied to a Sepharose 6B-Cl column (1.5×86 cm). The gp70R-delta protein was eluted at a flow rate of 6.6 ml/hr with 4M urea, 50 mM sodium borate, pH 9.0. Fractions (5.3 ml/fraction) were collected and the gp70R-delta was determined by protein assay and SDS-polyacrylamide electrophoresis to be in fractions 13–15.

The citraconylation of gp70R-delta was reversed by dialyzing 5 ml of alkylated, citraconylated gp70R-delta (1.0 mg/ml) against 6M urea in 50 mM sodium citrate, pH 5.5 for 48 hours at room temperature. The gp70R-delta was dialyzed against 6 M urea in 100 mM sodium bicarbonate, pH 8.0 and the protein concentration adjusted to 0.8 mg/ml prior to absorption to aluminum hydroxide.

Procedure III

A modification of the above purification of alkylated, citraconylated gp70R-delta was developed. Briefly, alkylated, citraconylated gp70R-delta is modified and dialyzed against 50 mM sodium borate, pH 9.0 as described above. Urea was added to a final concentration of 8.0M. The protein was concentrated by ultrafiltration with a PM-30 membrane to yield 2.5 mg protein/ml. The protein solution was applied to a Sephacryl S-400 column (1.5×90 cm) in a 50 mM sodium borate buffer, pH 9.0 containing 8M urea and eluted with the same buffer. Fractions (2.9 ml/fraction) were collected and fractions 34–37 containing gp70R delta were pooled. Twenty-one mg of the protein from these fractions were diluted to a final concentration of 4M urea with 50 mM sodium borate, pH 9.0 and applied to a DEAE-TSK column (1.5×11 cm). The protein was eluted with a linear gradient of NaCl (0–0.5M) in 50 mM sodium borate, pH 9.0 containing 4M urea. Three ml fractions were collected. Fractions 89–95 containing gp70R-delta were pooled and 15 mg of gp70R-delta was recovered.

EXAMPLE 12

Immunization with Aluminum Hydroxide-Absorbed gp70R-delta

Aluminum hydroxide which has been found to have an adjuvant effect for many proteins and is coolly used in vaccines was used as a carrier for gp70R-delta. gp70Rdelta prepared by procedure I of Example 11 above absorbs tightly to 10% aluminum hydroxide in the presence of 50 mM Tris-Cl, pH 8.0 containing 6M urea. Approximately 3 μg gp70R-delta were absorbed per 100 μg aluminum hydroxide. The gp70R-delta absorbed to the aluminum hydroxide was washed with phosphate buffered saline (PBS), resuspended in PBS and used for immunization of animals.

Figure 13:
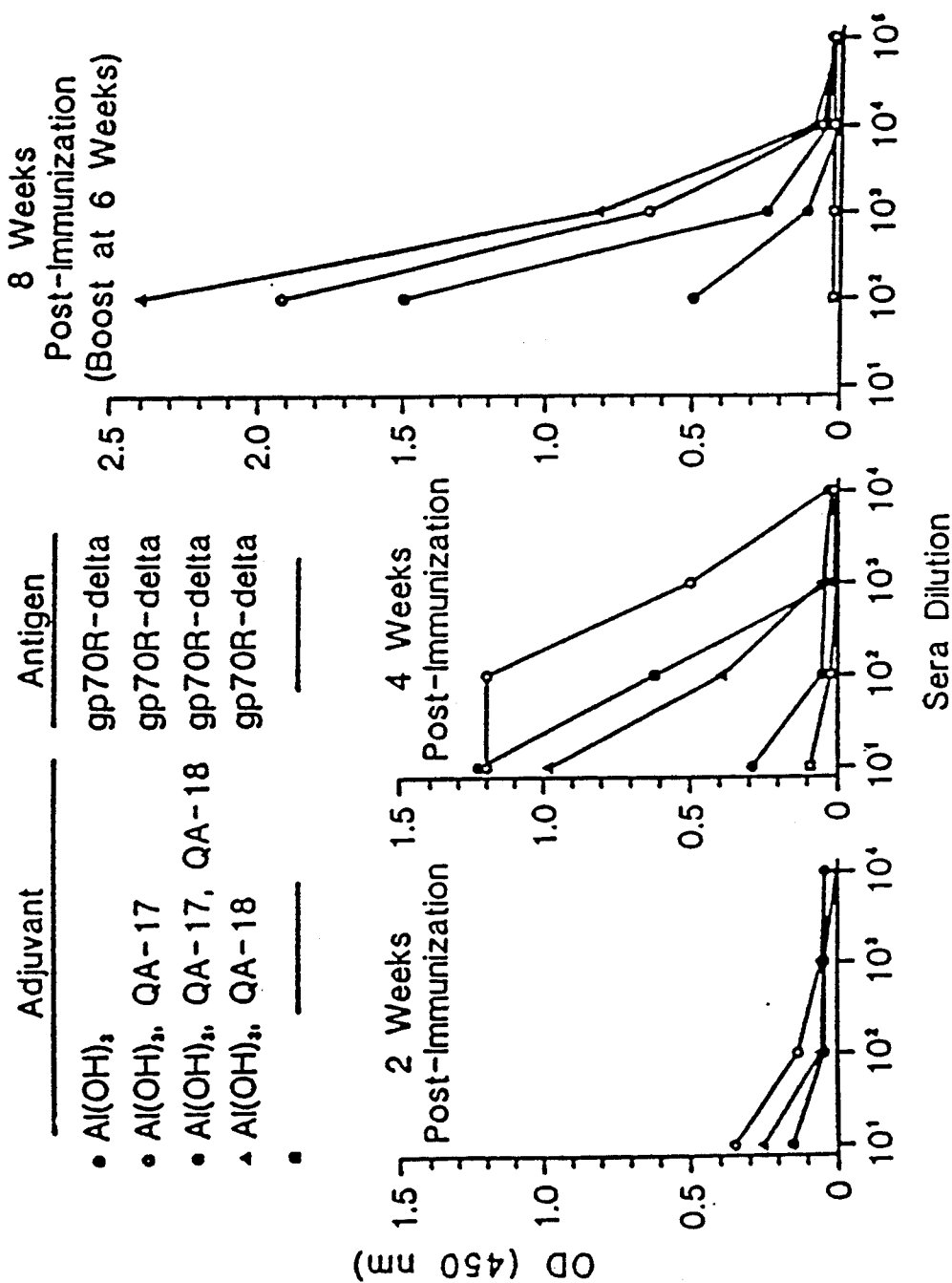
FIG. 13 shows the adjuvant effects of HPLC-purified adjuvants used in conjunction with $Al(OH)_3$, another adjuvant, on the immunization with the antigen gp70R-delta.

CD-1 mice (8–10 weeks old) were immunized intradermally with gp70R-delta absorbed to Al(OH)$_3$ in a total volume of 200 μl PBS in the presence and absence of HPLC-purified saponins QA-17 or QA-18 or a mixture of QA-17 and QA-18. Twenty to twenty-five μg of gp70R-delta were injected per dose. HPLC-purified saponins QA-17 or QA-18 or a mixture of QA-17 and QA-18 were used at a dry weight dose of 10 μg. Two mice were injected for each formulation. Mice were given a booster injection of gp70R-delta/aluminum hydroxide six weeks after the initial injection. Mouse sera was analyzed for reactivity to FEA, a FeLV subgroup A, at 2, 4, and 8 weeks post-immunization by an ELISA immunoassay. Four weeks following immunization, an anti-FeLV response elicited by the recombinant gp70-delta was observed. HPLC-purified saponin adjuvants QA-17 and QA-18 boost this response. The response was two orders of magnitude greater at four weeks post-immunization in the presence of QA-17 compared to immunization in the absence of saponin adjuvant. The results of this experiment are shown in FIG. 13.

Anti-FEA antibody was assayed by an ELISA assay. FEA virus (10 μg/ml in PBS) was absorbed to Immulon II plates overnight at 4° C. (100 μl/well). The plates were washed with PBS and nonspecific antibody binding was blocked by incubation for 1 hour with 10% normal goat serum in PBS (100 μl/well) at room temperature. Plates were then washed with 0.05% Tween-20 in distilled water. Sera was diluted in 10% normal goat serum in PBS and incubated for 1 hour at room temperature on the plate at serum dilutions of 10, $10^2$, $10^3$, and $10^4$ (100 μl/well). After washing the plates with 0.05% Tween-20 in distilled water, they were incubated for 30 minutes at room temperature with 100 μl/well of peroxidase-conjugated goat anti-mouse IgG (Boehringer-Mannheim) diluted 1/5000 in PBS. After washing the plates with 0.05% Tween-20 in distilled water, the amount of IgG-binding was determined by peroxidase reaction with 3,3',5,5'-tetramethylbenzidine from the absorbance at 450 nm determined on a Dynatech microliter plate reader.

EXAMPLE 13

Immunization with Aluminum Hydroxide-Absorbed Alkylated gp70R-delta

Figure 14:
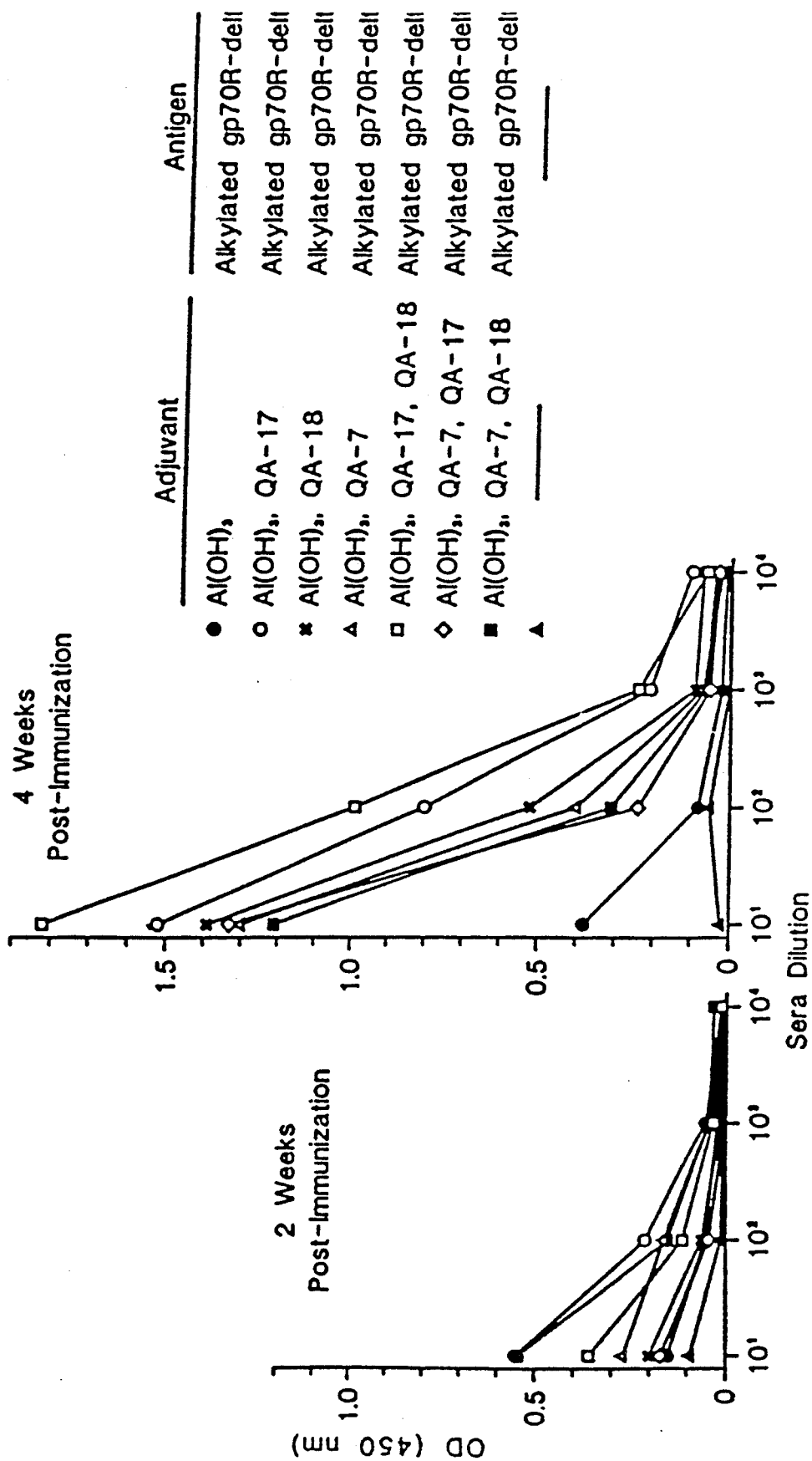
FIG. 14 summarizes the effects of HPLC-purified Quillaja saponins alone and in combination with each other and with another adjuvant on the immunization with the antigen alkylated gp70R-delta.

CD-1 mice (8–10 weeks old) were immunized intradermally with 15 μg/dose of alkylated gp70R-delta purified by procedure II of Example 11 (absorbed to aluminum hydroxide as described in Example 12) in 200 μl PBS. HPLC-purified adjuvants AQ-7, AQ-17, AQ-18 and mixtures of the three adjuvants were used at a dry weight dose of 10 μg. Three mice were injected for each formulation. Mouse sera was analyzed by ELISA at 2 and 4 weeks postimmunization for reactivity to FEA as described in Example 10. As with immunization with unmodified gp70R-delta shown in Example 10, immunization with alkylated gp70R-delta elicits an anti-FeLV viral response by four weeks post-immunization. HPLC-purified adjuvants QA-7, QA-17, QA-18 all increase the immune response as compared to immunization in the absence of the saponin adjuvants. QA-17 and mixtures of QA-17 and QA-18 induced the highest response, inducing endpoint titers almost two orders of magnitude greater than immunization in the absence of saponin adjuvants. The results of these experiments are summarized on FIG. 14.

EXAMPLE 14

Toxicity of QA-7, QA-17, QA-18, QA-19, QA-21, "Quil-A"

With crude Quillaja saponins, a major symptom of toxicity in mice appears as necrosis of the liver. Purified saponins were injected into mice to determine effects on the liver. Mice were injected intradermally with 150 μg each QA-7, QA-17, QA-18, QA-21 and "Quil-A", the crude saponin extract used as the raw material for the purification of the other components. Animals injected with QA-7, QA-17, QA-18, and QA-21 appeared mildly ill initially but appeared to recover fully within a few hours after injection. "Quil-A" caused severe symptoms which continued for 48 hours. All mice were sacrificed at 48 hours for post-mortem examination of the liver. "Quil-A" caused severe damage of the liver with multifocal areas of acute necrosis evident. QA-7, QA-17, QA-18, and QA-21 did not seem to significantly affect the liver. QA-17 and QA-18 were also tested in kittens with subcutaneous injection of 100 μg each at 8 and 10 weeks, with no toxicity observed clinically or in the blood chemistry. In contrast, "Quil-A" induced a pyrogenic response which persisted for several hours in kittens. Hence, the purified saponins appear to be less toxic than "Quil-A" in both mice and kittens indicating that the purification process separates these saponins from one or more toxic components present in a crude Ouillaja extract. One such toxic component has tentatively been identified as QA-19; dosages of 50 μg or greater were lethal in mice within a few days of injection. Further purification of QA-19 indicated that it could be separated into two peaks, QA-19a and QA-19b. QA-19a was lethal in mice at doses of 100 μg or greater whereas QA-19b was apparently nonlethal up to dose of 150 μg; hence, a synergistic effect to produce increased toxicity in the mixture of QA-19a and QA-19b cannot be ruled out. Preliminary screening of other minor peaks isolated from "Quil-A" indicates that other fractions may also be toxic. Hence, the purification protocols allow the separation of adjuvant-active saponins from similar but distinct compounds which are more toxic or which cochromatograph with toxic contaminants.

EXAMPLE 15

Figure 15:
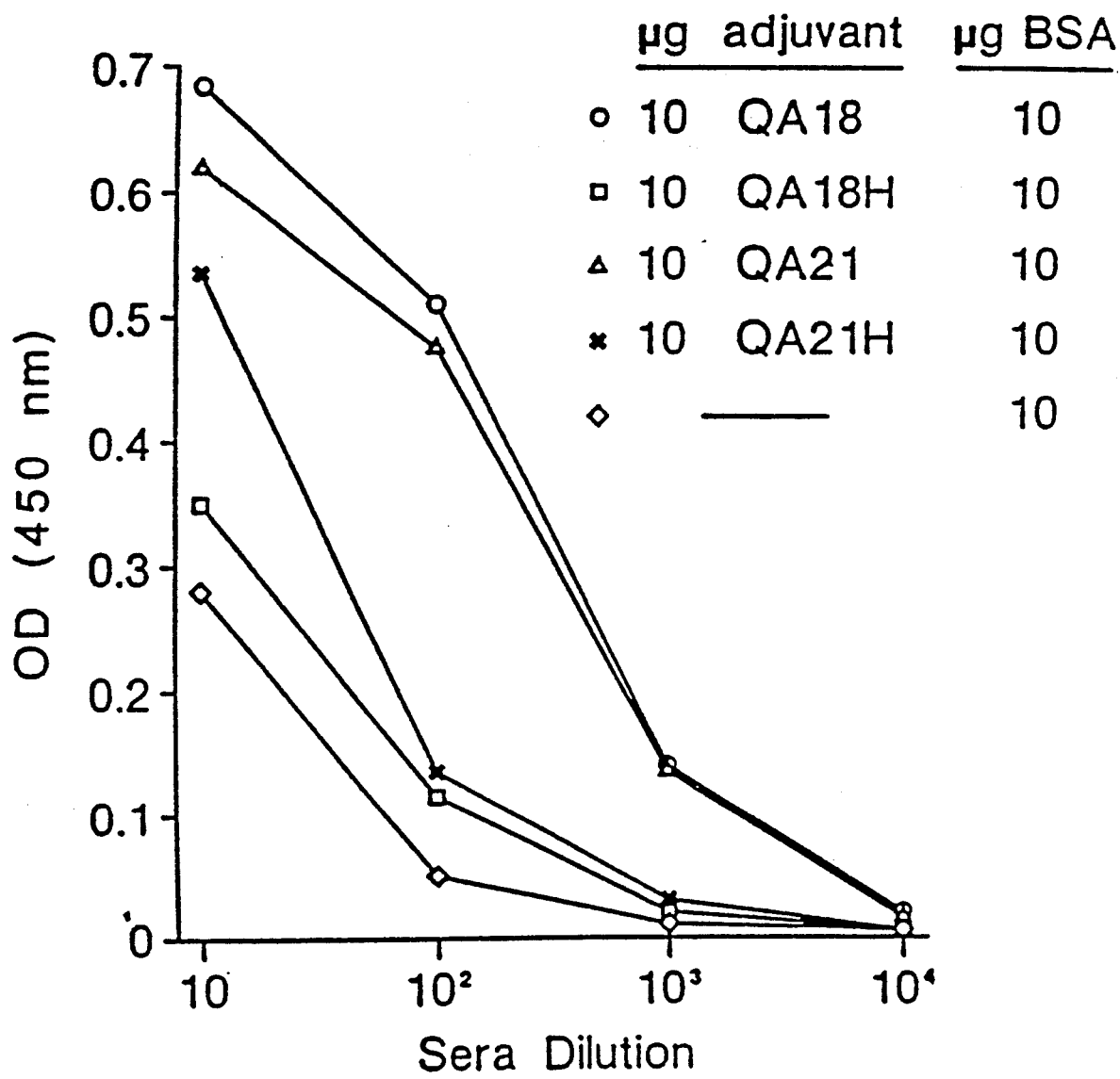
FIG. 15 shows a comparison of the adjuvant effects of QA-18, QA-18H, QA-21, and QA-21H on immunization with the antigen BSA.

QA-18H and QA-21H, prepared as described in Example 7, were tested for adjuvant effect with BSA in direct comparison with the unhydrolyzed original products QA-18 and QA-21 prepared as described in Examples 3 and 4. QA-18 and QA-21 increase the humoral immune response to BSA in mice by at least an order of magnitude by two weeks post-immunization. However, the hydrolysis products QA-18H and QA-21H at the same weight dosage do not increase the response significantly (FIG. 15). Hence, optimal adjuvant effect is observed with the intact saponins; the essential structure required for adjuvant activity is lost or altered when QA-18 and QA-21 are hydrolyzed to QA-18H and QA-21H, respectively.

The invention now being fully described, it will be apparent to one of ordinary skill in the art that many changes and modifications can be made thereto without departing from the spirit or scope of the invention as set forth below.

What is new and intended to be covered by Letters Patent of the United States is:

1. Substantially pure saponin purified from a crude *Quillaja saponaria* extract wherein said pure saponin is characterized by a single predominant peak which comprises 90% or more of the total area of all peaks of a chromatogram, excluding the solvent peak, when analyzed on reverse phase-HPLC on a Vydac $C_4$ column having 5 μm particle size, 330 Å pore, 4.6 mm ID×25 cm L in a solvent of 40 mM acetic acid in methanol/water (58/42; v/v) at a flow rate of 1 ml/mixture, and wherein said saponin has immune adjuvant activity and is less toxic when used as an adjuvant than said *Quillaja saponaria* extract.

2. Substantially pure QA-7 saponin purified from a crude *Quillaja saponaria* extract wherein said pure saponin is characterized by one predominant peak which comprises 90% or more of the total area of all peaks of a chromatogram, excluding the solvent peak, and having a retention time of approximately 9–10 minutes when analyzed on reverse phase HPLC on a Vydac $C_4$ column having 5 μm particle size, 330 Å pore, 4.6 mm ID×25 cm L in a solvent of 40 mM acetic acid in methanol/water (58/42; v/v) at a flow rate of 1 ml/minute.

3. The substantially pure QA-7 saponin of claim 2, wherein said saponin has immune adjuvant activity, and wherein said saponin is characterized by a carbohydrate content of about 35% per dry weight as assayed by anthrone, has a UV adsorption maxima of 205–210 nm, has a micellar concentration of 0.06% (w/v) in water and 0.07% in phosphate buffered saline, and causes no detectable hemolysis of sheep red blood cells at concentrations of 200 μg/ml.

4. The substantially pure QA-7 saponin of claim 3, wherein said carbohydrate content has a composition comprising the monosuccharides: terminal rhamnose, terminal xylose, terminal glucose, terminal galactose, 3-xylose, 3,4-rhamnose, 2,3-fucose, 2,3-glucuronic acid and apiose.

5. Substantially pure QA-21 saponin purified from a crude *Quillaja saponaria* extract wherein said pure saponin is characterized by one predominant peak which comprises 90% or more of the total area of all peaks of a chromatogram, excluding the solvent peak, and having a retention time of approximately 51minutes when analyzed on reverse phase-HPLC on a Vydac $C_4$ column having 5 μm particle size, 330 Å pore, 4.6 mm ID×25 cm L in a solvent of 40 mM acetic acid in methanol/water (58/42; v/v) at a flow rate of 1 ml/minute.

6. The substantially pure QA-21 saponin of claim 5, wherein said saponin has immune adjuvant activity, and wherein said saponin is characterized by a carbohydrate content of about 22% per dry weight as assayed by anthrone, has a UV absorption maxima of 205–210 nm, has a micellar concentration of about 0.03% (w/v) in water and 0.02% (w/v) in phosphate buffered saline, and causes hemolysis of sheep red blood cells at concentrations of 25 μg/ml or greater.

7. The substantially pure QA-21 saponin of claim 6, wherein said carbohydrate content has a composition comprising the monosaccharides: terminal rhamnose, terminal arabinose, terminal apiose, terminal xylose, 4-rhamnose, terminal glucose, terminal galactose, 2-fucose, 3-xylose, 3,4-rhamnose and 2,3-glucuronic acid.

8. A substantially pure QA-17 saponin purified from a crude *Quillaja saponaria* extract wherein said pure saponin is characterized by one predominant peak which comprises 90% or more of the total area of all peaks of a chromatogram, excluding the solvent peak, and having a retention time of approximately 35 minutes on reverse phase-HPLC on a Vydac $C_4$ column having 5 μm particle size, 330 Å pore, 4.6 mm ID×25 cm L in a solvent of 40 mN acetic acid in methanol/water (58/42; v/v) at a flow rate of 1 ml/minute.

9. The substantially QA-17 saponin of claim 8, wherein said saponin has immune adjuvant activity, and wherein said saponin is characterized by a carbohydrate content of about 29% per dry weight as assayed by anthrone, has a UV absorption maxima of 205–210 nm, has a micellar concentration of about 0.06% (w/v) in water and 0.03% (w/v) in phosphate-bufferred saline, and causes hemolysis of sheep red blood cells at concentrations of 25 μg/ml.

10. The substantially pure QA-17 saponin of claim 9, wherein said carbohydrate content has a composition comprising the monosaccharides: terminal rhamnose, terminal xylose, 2-fucose, 3-xylose, 3,4-rhamnose, 2,3-glucuronic acid, terminal glucose, 2-arabinose, terminal galactose and apiose.

11. A substantially pure QA-18 saponin purified from a crude *Quillaja saponaria* extract wherein said pure saponin is characterized by one predominant peak which comprises 90% or more of the total area of all peaks of a chromatogram, excluding the solvent peak, and having a retention time of approximately 38 minutes on reverse phase-HPLC on a Vydac $C_4$ column having 5 μm particle size, 330 Å pore, 4.6 mm ID×25 cm L in a solvent of 40 mM acetic acid in methanol/water (58/42; v/v) at a flow rate of 1 ml/minute.

12. The substantially QA-18 saponin of claim 11, wherein said saponin has immune adjuvant activity, and wherein said saponin is characterized by a carbohydrate content of about 25–26% per dry weight as assayed by anthrone, has a UV absorption maxima of 205–210 nm, has a micellar concentration of 0.04% (w/v) in water and 0.02% (w/v) in phosphate-buffered saline, and causes hemolysis of sheep red blood cells at concentrations of 25 μg/ml.

13. The substantially pure QA-18 saponin of claim 12, wherein said carbohydrate content has a composition comprising the monosaccharides: terminal rhamnose, terminal arabinose, terminal apiose, terminal xylose, terminal glucose, terminal galatose, 2-fucose, 3-xylose, 3,4-rhamnose and 2,3-glucuronic acid.

14. A method of enhancing an immune response to an antigen in an individual comprising administration of an amount of the substantially pure saponin adjuvants from any of claims 1–7 and 8–13 to said individual in an amount sufficient to enhance the immune response of said individual to said antigen.

15. A pharmaceutical composition useful for inducing the production of antibodies to an antigen in an individual comprising an immunogenically effective amount of an antigen and at least one substantially pure saponin as in any one of claims 1–7 and 8–13, wherein said substantially pure saponin is present in an amount sufficient to enhance the immune response of said individual to said antigen.

16. The pharmaceutical composition of claim 15, wherein said individual is a mammal.

* * * * *

UNITED STATES PATENT AND TRADEMARK OFFICE
CERTIFICATE OF CORRECTION

PATENT NO. : 5,057,540

DATED : October 15, 1991

INVENTOR(S) : Charlotte A. Kensil, et al

It is certified that error appears in the above-identified patent and that said Letters Patent is hereby corrected as shown below:

Column 10, line 32, "40 nM" should read "40 mM".

Column 11, Table 2, last line, under the heading "HPLC Fraction" there should be a dash " - " to denote that no fraction was included as adjuvant with the antigen.

Column 12, line 1, "QA-17" should read "QA-7".

Column 20, line 49, "coolly" should read "commonly".

Column 21, line 32, "microliter" should read as "microtiter".

UNITED STATES PATENT AND TRADEMARK OFFICE
CERTIFICATE OF CORRECTION

PATENT NO. : 5,057,540

DATED : October 15, 1991

INVENTOR(S) : Charlotte A. Kensil, et al

It is certified that error appears in the above-identified patent and that said Letters Patent is hereby corrected as shown below:

Column 21, lines 41 and 42, "AQ-7, AQ-17, AQ-18" should read "QA-7, QA-17, and QA-18".

Column 23, line 22, "monosuccharides" should read "monosaccharides".

Column 24, line 1, "mN" should read "mM".

Signed and Sealed this

First Day of June, 1993

*Attest:*

MICHAEL K. KIRK

*Attesting Officer*   Acting Commissioner of Patents and Trademarks

UNITED STATES PATENT AND TRADEMARK OFFICE
CERTIFICATE OF CORRECTION

PATENT NO. : 5,057,540
APPLICATION NO. : 07/573268
DATED : October 15, 1991
INVENTOR(S) : Charlotte A. Kensil and Dante J. Marciani It is certified that error appears in the above-identified patent and that said Letters Patent is hereby corrected as shown below:

At column 4, line 53, "330 Å" should be -- 300 Å --.

At column 5, line 66, "330 Å" should be -- 300 Å --.

At column 6, line 2, "330 Å" should be -- 300 Å --.

At column 6, line 18, "330 Å" should be -- 300 Å --.

At column 6, line 22, "330 Å" should be -- 300 Å --.

At column 6, line 39, "330 Å" should be -- 300 Å --.

At column 6, line 43, "330 Å" should be -- 300 Å --.

At column 6, line 59, "330 Å" should be -- 300 Å --.

At column 6, line 62, "330 Å" should be -- 300 Å --.

At column 9, line 43, "330 Å" should be -- 300 Å --.

At column 10, line 31, "330 Å" should be -- 300 Å --.

At column 12, line 56, "1980" should be -- 1988 --.

In claim 1, at column 22, line 63, "330 Å" should be -- 300 Å --.

In claim 2, at column 23, line 8, "330 Å" should be -- 300 Å --.

In claim 5, at column 23, line 33, "330 Å" should be -- 300 Å --.

In claim 8, at column 23, line 59, "330 Å" should be -- 300 Å --.

UNITED STATES PATENT AND TRADEMARK OFFICE
CERTIFICATE OF CORRECTION

PATENT NO. : 5,057,540
APPLICATION NO. : 07/573268
DATED : October 15, 1991
INVENTOR(S) : Charlotte A. Kensil and Dante J. Marciani It is certified that error appears in the above-identified patent and that said Letters Patent is hereby corrected as shown below:

In claim 11, at column 24, line 25, "330 Å" should be -- 300 Å --.

Signed and Sealed this

Thirty-first Day of July, 2007

JON W. DUDAS
*Director of the United States Patent and Trademark Office*